United States Patent
Tsukuda

(10) Patent No.: US 9,528,149 B2
(45) Date of Patent: Dec. 27, 2016

(54) METHOD FOR ANALYZING MULTIPLE NUCLEIC ACID TARGETS

(71) Applicant: Panasonic Intellectual Property Management Co., Ltd., Osaka (JP)

(72) Inventor: Masahiko Tsukuda, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 15/049,053

(22) Filed: Feb. 20, 2016

(65) Prior Publication Data
US 2016/0265030 A1    Sep. 15, 2016

(30) Foreign Application Priority Data

Mar. 10, 2015 (JP) .................................. 2015-047525

(51) Int. Cl.
*C12Q 1/68* (2006.01)

(52) U.S. Cl.
CPC .................................. *C12Q 1/686* (2013.01)

(58) Field of Classification Search
CPC ....... C12Q 1/68; C12Q 1/6802; C12Q 1/6806; C12Q 1/6809; C12Q 1/6811; C12Q 1/6813; C12Q 1/6818; C12Q 1/682; C12Q 1/6825; C12Q 1/686; C12Q 1/6853; C12Q 1/6844
See application file for complete search history.

(56) References Cited

U.S. PATENT DOCUMENTS

| | | | | |
|---|---|---|---|---|
| 2008/0038810 A1* | 2/2008 | Pollack | ............. | B01L 3/502761 435/283.1 |
| 2008/0314761 A1* | 12/2008 | Herminghaus | ....... | B01F 3/0807 205/687 |
| 2009/0217742 A1* | 9/2009 | Chiu | ................ | G01N 27/44717 73/61.55 |
| 2011/0053798 A1* | 3/2011 | Hindson | .............. | C12Q 1/6844 506/12 |
| 2011/0217736 A1* | 9/2011 | Hindson | ................. | C12P 19/34 435/91.2 |

(Continued)

FOREIGN PATENT DOCUMENTS

| | | |
|---|---|---|
| JP | 6-500021 | 1/1994 |
| JP | 2013-524169 | 6/2013 |

(Continued)

*Primary Examiner* — Shogo Sasaki
(74) *Attorney, Agent, or Firm* — McDermott Will & Emery LLP

(57) ABSTRACT

A detection device includes a PCR processor for conducting a PCR process on a first drop to a fourth drop flowing in a flow channel, a boundary detector for detecting intensities of fluorescence outputted from the first drop to the fourth drop after the PCR process and acquiring boundaries between the first drop to the fourth drop flowing in a flow channel based on the intensities of fluorescence, and a detector for acquiring a number of the second drop and the fourth drop having an intensity of fluorescence greater than or equal to a first threshold based on the intensity of fluorescence and boundaries between the first drop to the fourth drop, and detecting whether or not the objective nucleic acid target includes at least one selected from the group consisting of a first nucleic acid target and a second nucleic acid target based on the number of the second drop and the fourth drop.

12 Claims, 14 Drawing Sheets

(56) References Cited

U.S. PATENT DOCUMENTS

| | | | | |
|---|---|---|---|---|
| 2011/0311978 A1* | 12/2011 | Makarewicz, Jr. | ... B01F 3/0807 | 435/6.12 |
| 2012/0171683 A1* | 7/2012 | Ness | ........ C12Q 1/6806 | 435/6.12 |
| 2012/0190033 A1* | 7/2012 | Ness | .......... B01L 3/021 | 435/6.12 |
| 2012/0194805 A1* | 8/2012 | Ness | .......... G01N 21/05 | 356/213 |
| 2012/0219947 A1* | 8/2012 | Yurkovetsky | ....... B01F 5/0471 | 435/6.11 |
| 2012/0264646 A1* | 10/2012 | Link | ........ B01F 5/0646 | 506/11 |
| 2012/0309002 A1* | 12/2012 | Link | ...... C12N 15/1068 | 435/6.11 |
| 2012/0329664 A1* | 12/2012 | Saxonov | ......... C12Q 1/6851 | 506/9 |
| 2013/0040841 A1* | 2/2013 | Saxonov | ......... C12Q 1/6851 | 506/9 |
| 2013/0084572 A1* | 4/2013 | Hindson | ......... G01N 21/6428 | 435/6.12 |
| 2013/0099018 A1* | 4/2013 | Miller | ........ C12Q 1/6806 | 239/10 |
| 2013/0109575 A1* | 5/2013 | Kleinschmidt | ... G01N 33/5302 | 506/2 |

FOREIGN PATENT DOCUMENTS

| | | |
|---|---|---|
| WO | 92/02638 | 2/1992 |
| WO | 2011/120006 | 9/2011 |

* cited by examiner

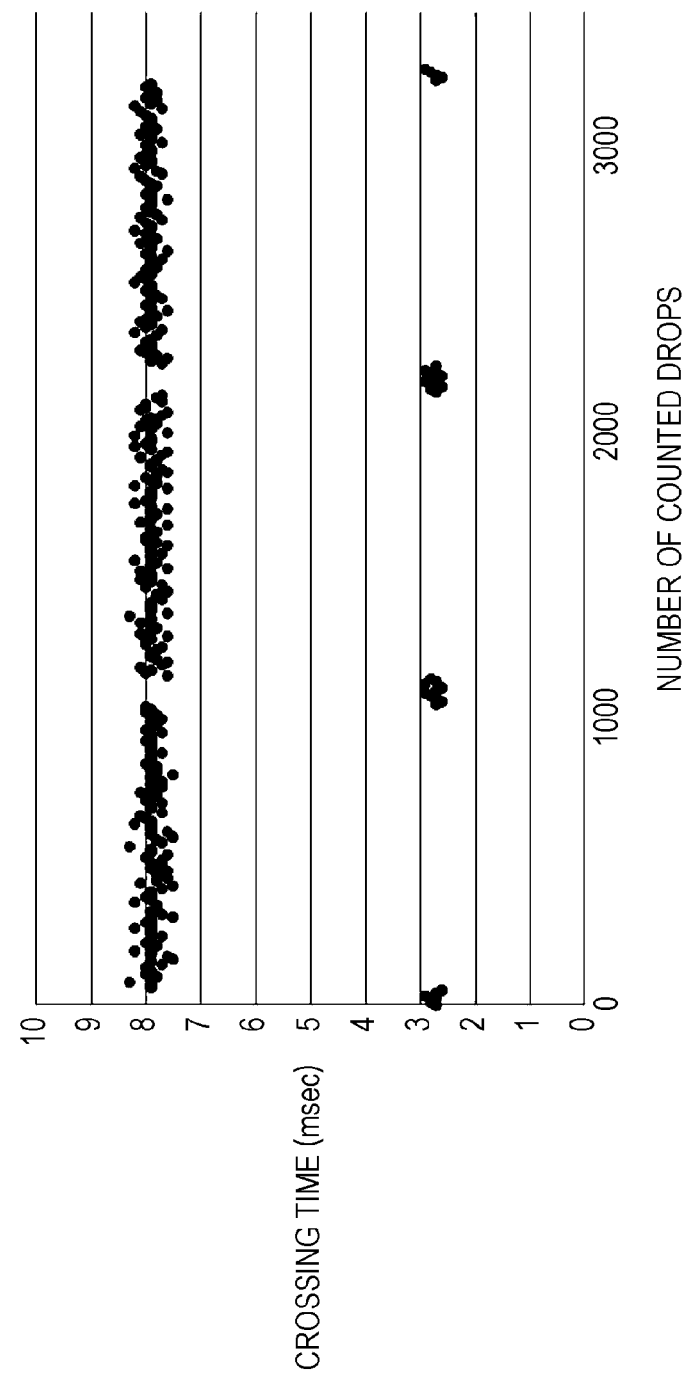

METHOD FOR ANALYZING MULTIPLE NUCLEIC ACID TARGETS

BACKGROUND

1. Technical Field

The present disclosure relates to a method for analyzing nucleic acid targets.

2. Description of the Related Art

As a basic technique for realizing this, a method of amplifying a desired nucleic acid target in nucleic acid such as DNA or RNA to such a quantity that is required for detection with a technique called PCR (polymerase chain reaction), and detecting the amplified target is generally known. As an advanced form of this technique, a quantitative analytic technique called qPCR (quantitative PCR) is generally used. Such a quantitative analytic technique for a nucleic acid target is introduced into a small reactor in a microfluidic chip.

PTL 1 discloses a basic method for realizing qPCR for quantitative analysis of gene. PTL 1 discloses a method that includes bringing a sample of single-stranded DNA into contact with an oligo nucleotide having a sequence that is complementary to a first region of the sequence chain of a target DNA (shorter DNA/RNA sequence), and with a labeled oligonucleotide including a sequence that is complementary to a second region of the sequence chain of the same target DNA, to form a mixture of double-stranded complex under the condition that causes hybridization; cutting the annealed labeled oligonucleotide by 5'→3' nuclease activity to liberate the labeled fragment; and detecting the liberated labeled fragment. When a fluorescent dye and a quencher are used as the labeled fragment of the labeled oligonucleotide, fluorescence is emitted only after the labeled fragment is liberated. Therefore, the intensity of fluorescence increases by repetition of this process. In general, the condition of causing hybridization, the condition of causing nuclease activity and so on are realized by exposing an analyte under a certain temperature condition. Accordingly, repeating the aforementioned process means repeating predetermined temperature rise and fall (temperature cycle) on the analyte. By detecting the intensity of fluorescence with a photo detector, and examining the relation between the number of repetition of the aforementioned process (the number of temperature cycles) and the intensity of fluorescence, it is possible to analyze the degree of the objective sequence chain of the target DNA contained in the analyte. In the case of detecting targets of multiple sites per analyte, it becomes possible to conduct separation and analysis according to the difference in fluorescent wavelength in the photo detector by preparing labeled oligonucleotides that are complementary to the respective sequence chains, and differentiating the material and wavelength of the fluorescent dye which is to be a label among the different labeled oligonucleotides.

PTL 2 discloses one exemplary method for realizing the technique of quantitatively analyzing gene. In particular, an improved technique of a high throughput assay based on the emulsification technique is disclosed. Disclosed is a method of producing drops each functioning as an independent reaction chamber for biochemical reaction by the emulsification technique, and treating and assaying individual subcomponents (cell, nucleic acid, protein etc.) by using these drops.

By suspending water drops composed of DNA/RNA and so on in oil, it is possible to produce an oil-in-water emulsion. By stabilizing the emulsion with a surfactant, it is possible to reduce or eliminate binding of drops during heating, cooling and transportation, and thus it is possible to carry out a temperature cycling conducted in the PCR technique or the like. Therefore, amplification of single copy of a nucleic acid target molecule in drops by PCR is conducted by using an emulsion. Among these drops, drops that are positive to a specific target are analyzed according to the Poisson statistics, and the concentration of the target in the sample can be estimated. In the assay using drops, whether the reaction such as amplification occurs can be recognized by using one or more than one kinds of fluorescent substances as a label in drops. By generating liquid drops, reacting the drops, and measuring light emitted from each drop, it may be possible to determine whether the target exists in the drop. By assigning discriminable different kinds of fluorescent substances to different targets respectively, it is possible to determine whether multiple different targets exist in each drop. In discriminating the multiple different targets as described above, it is general to employ a technique of using multiple kinds of fluorescent substances, namely dye materials emitting fluorescence of different wavelength, and discriminating the targets according to the fluorescence wavelength. PTL 2 discloses a method of using two kinds of fluorescent dyes and detecting them discriminately. Detection systems (each including a light source and a detector) respectively corresponding to a first dye and a second dye are provided, and drops are detected alternately by the detection system corresponding to the first dye and the detection system corresponding to the second dye while the drops pass through the detection area of the flow channel.

CITATION LIST

Patent Literatures

PTL 1: Japanese Patent No. 2,825,976
PTL 2: Japanese Translation of PCT Publication 2013-524169

However, in the conventional constitution, when multiple nucleic acid targets are intended to be detected simultaneously in nucleic acid such as DNA/RNA, it is necessary to conduct separation and detection by preparing reaction chemical solutions such as primers, probes and the like having nucleotide sequences complementary to the respective base sequences of the nucleic acid targets, and varying the fluorescent dye that modifies the primer, probe and the like for each nucleic acid target. The light sources for exciting the respective fluorescent dyes, and the optical systems for detecting the fluorescent wavelength of the respective fluorescent dyes are required. As the number of kinds of nucleic acid targets to be detected simultaneously increases, disadvantageously, preparation of the corresponding fluorescent dyes and optical systems for detecting fluorescence are complicated.

SUMMARY

One non-limiting and exemplary embodiment provides a method for analyzing multiple nucleic acid targets with a small and low-cost constitution without requiring a complicated optical system for detecting fluorescence even when the number of kinds of nucleic acid targets to be detected simultaneously increases.

In one general aspect, the techniques disclosed here feature a method for detecting first nucleic acid targets and second nucleic acid targets using a microfluidic chip, the method comprising:

(a) installing the microfluidic chip in a detection device, wherein
   the detection device comprises a PCR processor, a PCR reactor, a fluorescence detector, and a detect circuitry,
   the microfluidic chip comprises a first flow channel, a second flow channel, a third flow channel, a fourth flow channel, and a fifth flow channel, wherein
   the fourth flow channel is connected with one end of the first flow channel, one end of the second flow channel, and one end of the third flow channel,
   the PCR reactor is located between the fourth flow channel and the fifth flow channel,
(b) (i) supplying from another end of the first flow channel a first aqueous solution, a first oil, and a second aqueous solution in this order, (ii) supplying from another end of the second flow channel a sample aqueous solution, and (iii) supplying a second oil from another end of the third flow channel, thereby causing a first drop, a second drop, a third drop and a fourth drop to pass through the fourth flow channel in this order, wherein
   the first drop is made from the first aqueous solution and the sample aqueous solution,
   the second drop is made from the sample aqueous solution,
   the third drop is made from the second aqueous solution and the sample aqueous solution,
   the fourth drop is made from the sample aqueous solution,
   the first aqueous solution has a first DNA having a complementary sequence to the first nucleic acid target, the first DNA is modified with a first fluorescent dye, and
   the second aqueous solution has a second DNA having a complementary sequence to the second nucleic acid target, the second DNA is modified with a second fluorescent dye,
(c) subjecting the first drop to the fourth drop which have passed through the fourth flow channel and reached the PCR reactor, to a PCR process with the PCR processor, and causing the first drop to the fourth drop which have subjected to the PCR process to pass through the fifth flow channel,
(d) detecting intensities of fluorescence outputted from the first drop to the fourth drop flowing in the fifth flow channel with the fluorescence detector,
(e) acquiring boundaries between the first drop to the fourth drop flowing in the fifth flow channel based on the intensities of fluorescence, and
(f) acquiring a number of the second drop and the fourth drop having an intensity of fluorescence greater than or equal to a first threshold based on the intensity of fluorescence and the boundaries between the first drop to the fourth drop, and
   detecting whether or not the sample aqueous solution include at least one selected from the group consisting of the first nucleic acid target and the second nucleic acid target based on the number of the second drop and the fourth drop with the detect circuitry.

According to the method for analyzing multiple nucleic acid targets of the present disclosure, even when the number of nucleic acid targets to be detected simultaneously increases, it is possible to use a fluorescent dye of the same wavelength as the fluorescent dye that modifies the reaction chemical solutions reacting one-to-one with the nucleic acid targets without complicating the flow channel constitution of the microfluidic chip. Therefore, it is possible to realize an optical waveguide that detects fluorescence with a simple constitution. Accordingly, it is possible to provide a small and low-cost device constitution.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

It should be noted that general or specific embodiments may be implemented as a system, a method, an integrated circuit, a computer program, a storage medium, or any selective combination thereof.

BRIEF DESCRIPTION OF THE DRAWINGS

FIG. 10 is a distribution chart showing the distribution of crossing time of a drop in Example 1;

DETAILED DESCRIPTION

Figure 1:
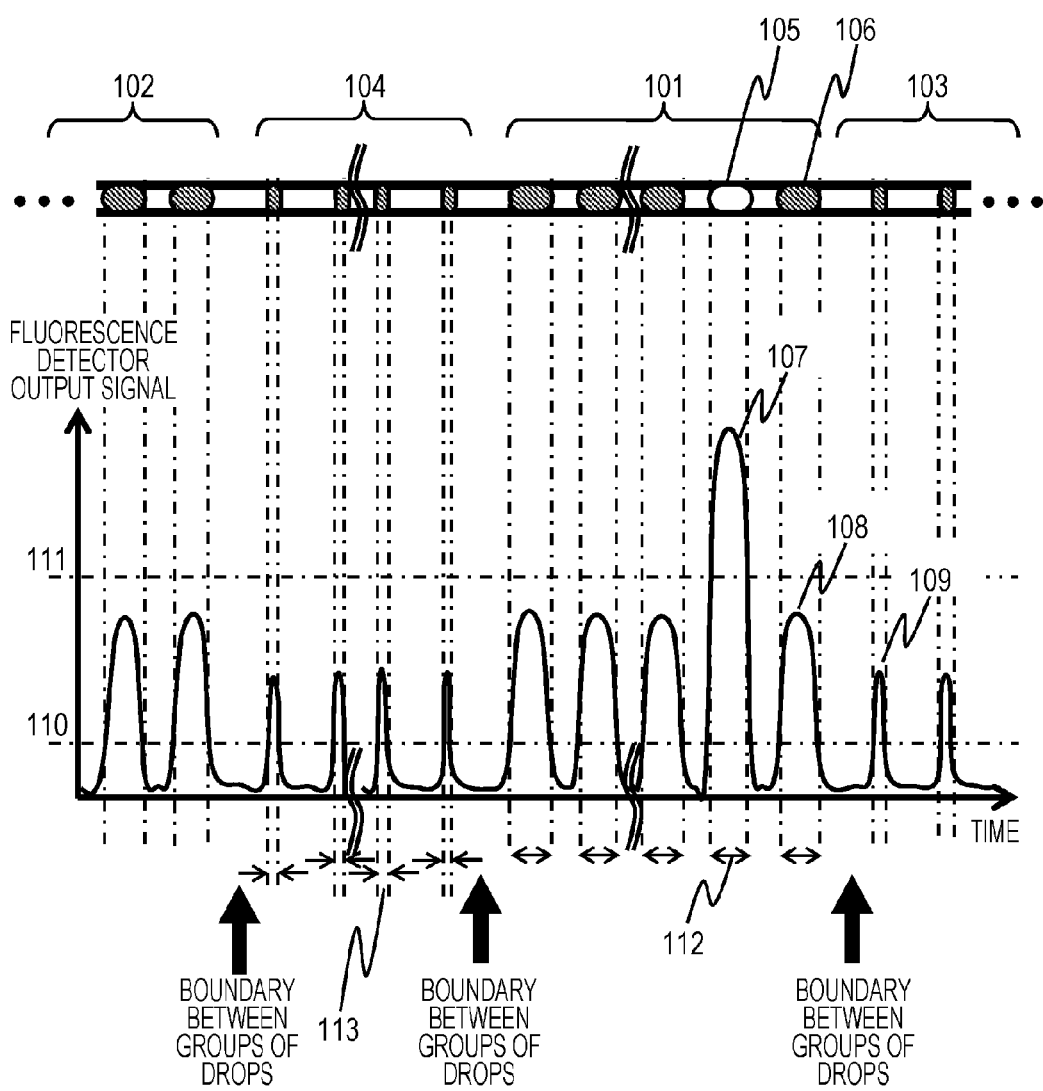
FIG. 1 includes a schematic diagram showing a plurality of groups of drops flowing in one flow channel of an optical waveguide of a microfluidic chip (upper stage) and one example of an output signal measured for the plurality of groups of drops (lower stage)

A gene screening method will be described. Gene is a major factor carrying genetic information of an organism, and is encoded in a base sequence of nucleic acid such as DNA or RNA as a medium in any organisms. Recently, the diversity analysis and the expression analysis of gene has outstandingly developed in associated with the improvement in gene diagnostic technology. Particularly in medical fields, the relationship between the genetic information and the disease attracts attentions. For example, analysis of information of individual genes (base sequence of DNA or RNA of a specific site) in association with diseases has made it possible to conduct an appropriate therapy or medication for each individual patient (tailor-made medical treatment). In the tailor-made medical treatment, the on-site diagnosis is most desired, and a rapid, convenient technique with high POCT (Point of Care Testing) property is required. For this reason, it is strongly demanded to realize a device capable of extracting and amplifying nucleic acid such as DNA or RNA containing a gene to be analyzed from a sampled analyte such as blood, and capable of detecting the information of the base sequence of the nucleic acid or the quantity of the nucleic acid rapidly and conveniently. In this context, nucleic acid to be analyzed is called a nucleic acid target. The term nucleic acid target implicates part of a base sequence of DNA or RNA, and short nucleic acid fragments such as messenger RNA (mRNA) and microRNA (miRNA) contained in blood or body fluid.

As one measure that meets the aforementioned demands, a device called µTAS (µ Total Analysis Systems) or LoC (Lab on Chip) attracts attention in recent years. µTAS or LoC is a device in which a micro flow channel and a port having a micro structure on the order of micrometer or nanometer is provided in a substrate, and various operations such as mixing of substances, extraction, purification, chemical reaction and analysis are conducted in the structure, and it has been partially brought into practical use. These devices, in which diverse operations are conducted in the micro structure, are advantageous to similar devices of ordinary size that are used in so-called specialized laboratories, analytical facilities in that the using amounts of a sample and a reagent are significantly small, the analytical time is short, and the sensitivity is high. Also a small device constitution can be realized, and with such a device, on-site analysis can be realized by using the device carried there, as well as analysis in a specialized laboratory. A structure having a micro structure including a micro flow channel and a port in a substrate, and equipped with various functions, manufactured for the aforementioned purpose is generally called a microfluidic chip or a micro fluid device.

For analyzing a nucleic acid target in an analyte in a short time by using a microfluidic chip, it is demanded to incorporate in the chip the functions of extraction, amplification, and detection of nucleic acid including the nucleic acid target to be detected. In particular, for obtaining more information in a short time, it is demanded to analyze multiple analytes at once in the same chip, or to amplify and detect multiple nucleic acid targets contained in one analyte (multiplex amplification and detection). Also depending on the use, it is demanded to analyze the quantity of a nucleic acid target contained in an analyte (quantitative analysis).

Hereinafter, a microfluidic chip and a method for analyzing nucleic acid targets according to exemplary embodiments of the present disclosure will be described with reference to attached drawings.

First Exemplary Embodiment

Figure 3A:
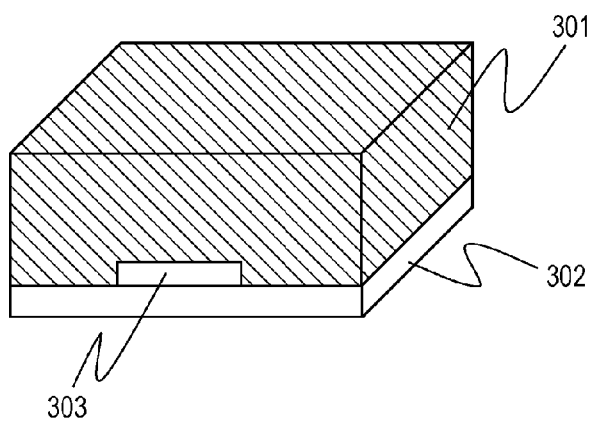
FIG. 3A is a perspective view of a cut out partial section of a flow channel of a microfluidic chip according to a first exemplary embodiment.
Figure 3B:
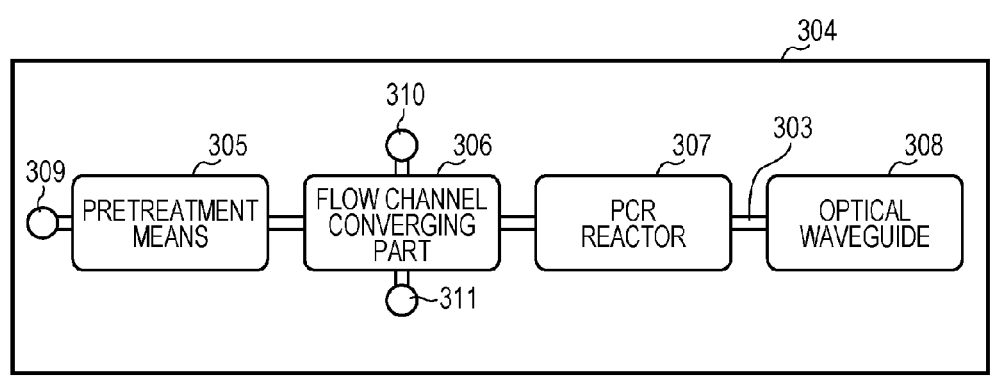
FIG. 3B is a schematic diagram showing one exemplary constitution of a microfluidic chip.

A microfluidic chip for analyzing multiple nucleic acid targets in a first exemplary embodiment of the present disclosure will be described with reference to drawings. FIG. 3A is a perspective view showing an external appearance of a microfluidic chip according to the first exemplary embodiment, and FIG. 3B is a schematic diagram showing one exemplary constitution of the microfluidic chip. The microfluidic chip includes at least a first flow channel adapted for a reaction chemical solution and a first oil to flow, a second flow channel adapted for a sample solution containing nucleic acid to flow, a third flow channel adapted for a second oil to flow, a flow channel converging part in which a group of drops containing a reaction chemical solution and a group of drops not containing a reaction chemical solution are generated, a fourth flow channel adapted for the generated groups of drops to flow, a nucleic acid amplifier for amplifying nucleic acid that can be contained in each drop in a group of drops, a fifth flow channel adapted for the group of drops having passed the nucleic acid amplifier to flow, and an optical waveguide capable of taking out transmitted light or reflected light of a group of drops in the fifth flow channel outside.

The first flow channel, the second flow channel, and the third flow channel converge at the flow channel converging part, and thus a group of drops containing a reaction chemical solution and a group of drops not containing a reaction chemical solution are generated depending on the kind of liquid supplied from the first flow channel.

A reaction chemical solution library has a flow channel retaining multiple reaction chemical solutions (for example, a first reaction chemical solution, and a second reaction chemical solution). For example, in the flow channel, oil is disposed between the first reaction chemical solution and the second reaction chemical solution, and the reaction chemical solution library retains the first reaction chemical solution and the second reaction chemical solution separately.

The multiple reaction chemical solutions each react with different nucleic acid targets in one-to-one correspondence, and are modified with a fluorescent dye.

The reaction chemical solution library is not necessarily provided in the microfluidic chip. The first flow channel should be supplied with the reaction chemical solution and the first oil from the reaction chemical solution library as is necessary.

In one flow channel (in the fifth flow channel), multiple drops containing amplified nucleic acid pass through in the same order as they are generated. The fifth flow channel is defined by a material that can transmit light from outside to the drops containing amplified nucleic acid, and can take out the transmitted light having transmitted the drops, or reflected light that is reflected after transmission through the drops outside.

Hereinafter, the reaction chemical solution library and the microfluidic chip will be described.

<Reaction Chemical Solution Library>

Figure 2:
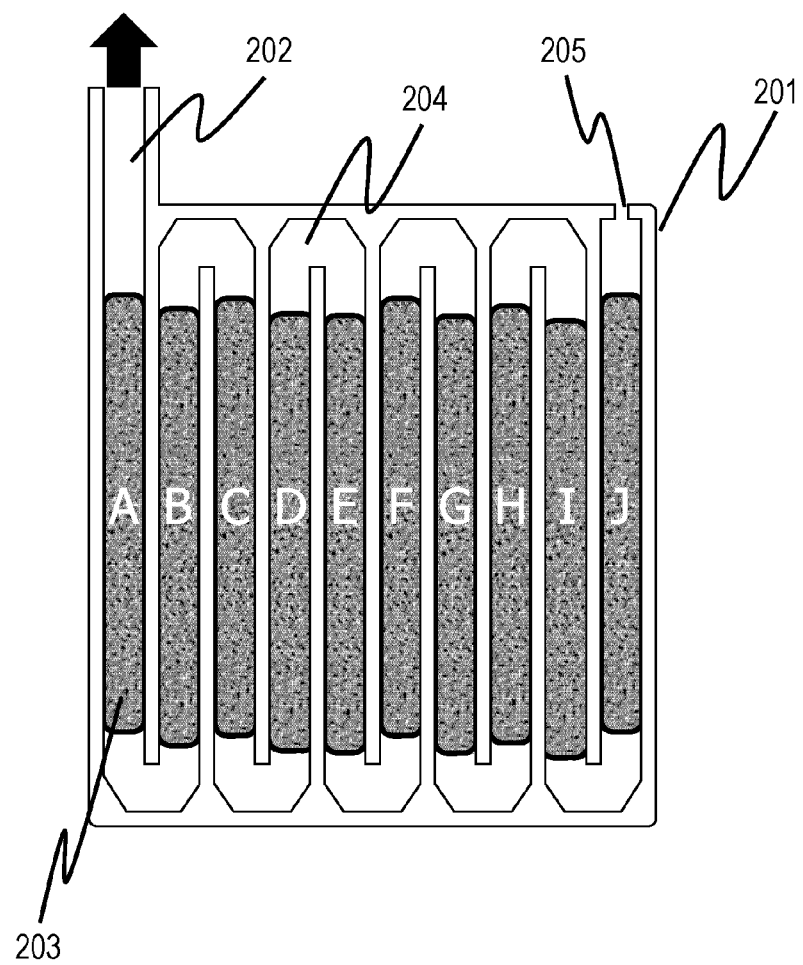
FIG. 2 is a schematic diagram showing one exemplary constitution of a reaction chemical solution library.

FIG. 2 is a schematic diagram showing one exemplary constitution of a reaction chemical solution library. When different multiple nucleic acid targets are analyzed, it is necessary to prepare reaction chemical solutions each containing a primer and a probe having base sequences complementary to the base sequence of each nucleic acid target, or an enzyme for amplifying the nucleic acid target individually. Chemical solution tank 201 has such a shape that one thin flow channel extends toward outlet 202 by means of the partitions disposed in the interior, and in the flow channel, reaction chemical solution 203 is retained. As shown in the drawing, oil (first oil) 204 is enclosed and retained between the different multiple reaction chemical solutions (hatched parts in the drawing) that react with different nucleic acid targets so that they do not mingle together. Also air hole 205 is provided besides outlet 202. Air hole 205 is closed during storing the chemical solution, and before actual use, air hole 205 is opened, and the reaction chemical solution and the oil in chemical solution tank 201 are sequentially supplied to the microfluidic chip through outlet 202. By employing this constitution, it is possible to supply the multiple reaction chemical solutions sequentially while they do not mingle together through outlet 202 of chemical solution tank 201 to the microfluidic chip situated ahead. In other words, a reaction chemical solution library capable of supplying multiple reaction chemical solutions is configured.

By using this reaction chemical solution library, different multiple reaction chemical solutions and oil are alternately supplied to the flow channel formed in the microfluidic chip connected ahead outlet 202 in the manner of reaction chemical solution A, oil, reaction chemical solution B, oil, and reaction chemical solution C. FIG. 2 shows the case of including ten kinds of reaction chemical solutions A to J; however, the number of kinds is arbitrary in the present disclosure as long as two or more kinds of reaction chemical solutions are included. By employing the constitution that two or more kinds of reaction chemical solutions are retained while they are separated by oil, it is possible to respond in the same manner for the case where the number of kinds of reaction chemical solutions increases or decreases. While a thin single flow channel is formed by providing walls in chemical solution tank 201 in this context, the shape of chemical solution tank 201 is not limited to this, and other shape will not influence on the effect as long as different multiple reaction chemical solutions and oil are retained alternately and the reaction chemical solutions and oil are supplied alternately through the outlet of the chemical solution tank. For example, one thin tubular tube may be introduced into the chemical solution tank, and the reaction chemical solutions and oil may be enclosed alternately in the tube.

<Microfluidic Chip>

FIG. 3A and FIG. 3B are diagrams showing the outline of the microfluidic chip in the first exemplary embodiment. FIG. 3A is a perspective view of a cut out partial section of a flow channel of a microfluidic chip. The microfluidic chip has such a structure that glass plate 302 or the like is bonded with a base material such as Si substrate 301. The base material such as Si substrate 301 is engraved in its surface into predetermined width and depth by etching or the like technique, and is formed with a groove which is to be a flow channel for allowing liquid to flow. By bonding glass plate 302 or the like with the surface of the base material such as Si substrate 301 in which the groove is formed, flow channel 303 in which a sample, a reaction chemical solution and the like flow is formed. By using the flow channel made in this manner, it becomes possible to allow a sample containing nucleic acid such as blood or body fluid to flow, and to allow the reaction chemical solution supplied from the chemical solution tank shown in FIG. 2 to flow. Also by connecting or branching these flow channels, the liquids can be mixed or separated. Also it is possible to form an arbitrary shape such as a reactor that conducts various treatments on the base material in a similar process as described above. The microfluidic chip forms elements such as a reactor, and a flow channel connecting these elements, and makes it possible to automatically conduct various treatments while a small amount of liquid flows in a small chip by means of a pump and a valve. When the plate bonded with the base material such as a Si substrate is a material that transmits light such as a glass plate as shown in FIG. 3A, it is possible to irradiate the flow channel with light such as light of laser or lamp or to measure an optical signal of reflected light or fluorescence from the liquid flowing in the flow channel from the side of the glass plate. While the structure in which the Si substrate and the glass plate are bonded together is described herein, both of these may be formed of glass plates, and the reaction chemical solution or the sample flowing in the flow channel may be irradiated with light, and the light may be detected from both sides. At least one of the plates should be a material that transmits light such as laser or LED, or fluorescence from a fluorescent dye flowing in the flow channel.

As shown in FIG. 3B, microfluidic chip 304 in the first exemplary embodiment has pretreatment means 305, flow channel converging part 306, PCR reactor 307, and optical waveguide 308. The elements are linked by flow channel 303 in which liquid flows. Microfluidic chip 304 has analyte supply port 309 for inputting an analyte such as blood or body fluid, reaction chemical solution supply port 310 to which the chemical solution tank is connected for supplying the reaction chemical solution library, and oil supply port 311 for supplying oil for generation of drops. The details will be described later.

In pretreatment means 305, a sample solution containing nucleic acid which is an object to be examined is prepared from an analyte such as blood or body fluid. Pretreatment means 305 takes out nucleic acid by destroying cells and the like so as to conduct the later-described nucleic acid amplification treatment (PCR). Alternatively, pretreatment means 305 conducts filtering so as to supply only the substance required for examination to the later stage. In pretreatment means 305, any treatment can be conducted without influencing on the effect of the present disclosure as long as the sample solution is purified into the form that can be subjected to PCR in the later stage. The sample solution purified in pretreatment means 305 is fed to next flow channel converging part 306.

In flow channel converging part 306, drops and a group of drops are generated by using the reaction chemical solution and oil supplied from the chemical solution tank. Generation of drops and a group of drops in flow channel converging part 306 will be described later.

A group of drops generated in flow channel converging part 306 is supplied to next PCR reactor 307. In PCR reactor 307, a nucleic acid target is subjected to the nucleic acid amplification treatment (PCR). Since nucleic acid is amplified only in a drop containing a desired nucleic acid target, the interior of the drop containing a nucleic acid target is in the condition that fluorescence is emitted, and the interior of the drop not containing a nucleic acid target is in the condition that fluorescence is not emitted. The group of drops after PCR is fed to the next optical waveguide. Examples of the PCR reactor include a chamber and a heater.

The optical waveguide conducts optical detection on drops flowing through one flow channel (fifth flow channel). For example, the number of flowing drops is optically counted, and the crossing time of a drop, or oil between drops is measured, or a drop is irradiated with light that excites fluorescence and the intensity of fluorescence emitted from the drop is detected.

Figure 4A:
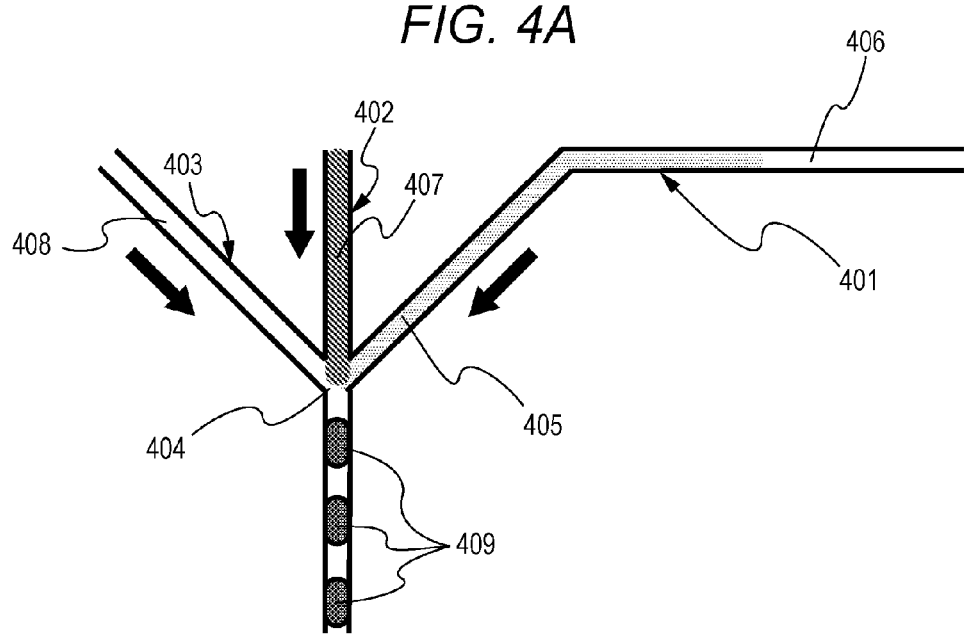
FIG. 4A is a schematic diagram showing one exemplary constitution of a flow channel converging part in the first exemplary embodiment.
Figure 4B:
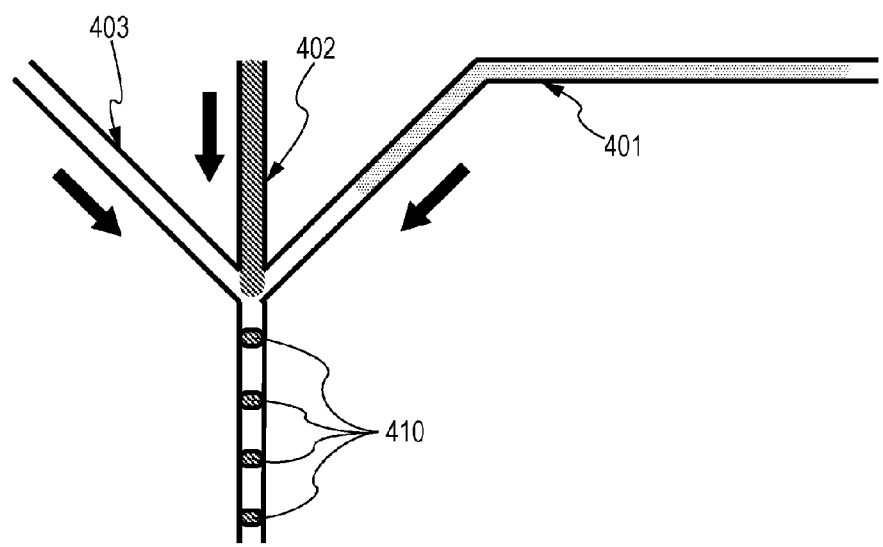
FIG. 4B is a schematic diagram showing one exemplary constitution of the flow channel converging part in the first exemplary embodiment.

FIG. 4A and FIG. 4B are schematic diagrams showing one exemplary constitution of flow channel converging part 306. As shown in FIG. 4A and FIG. 4B, one end of first supply flow channel 401, one end of second supply flow channel 402, and one end of third supply flow channel 403 are connected at junction 404 of the fourth flow channel. Flow channel converging part 306 means a general term for first supply flow channel 401, second supply flow channel 402, third supply flow channel 403, and fourth flow channel including junction 404.

In first supply flow channel 401, multiple reaction chemical solutions 405 and first oil 406 situated between multiple reaction chemical solutions 405 flow. FIG. 4A shows the state that reaction chemical solution 405 has flown to junction 404 from first supply flow channel 401. FIG. 4B shows the state that first oil 406 has flown to junction 404 from first supply flow channel 401.

The other end of first supply flow channel 401 connects with the chemical solution tank shown in FIG. 2. Multiple reaction chemical solutions 405 and first oil 406 situated between multiple reaction chemical solutions 405 contained in the chemical solution tank are supplied from the other end of first supply flow channel 401. Specifically, they are supplied to first supply flow channel 401 in the order of the first reaction chemical solution, first oil 406, and the second reaction chemical solution. The first reaction chemical solution and the second reaction chemical solution are included in multiple reaction chemical solutions 405. For example, first supply flow channel 401 may have a pump for supplying a liquid including multiple reaction chemical solutions 405. The other end of first supply flow channel 401 corresponds to reaction chemical solution supply port 310.

From the other end of second supply flow channel 402, a sample solution containing nucleic acid that is to be examined is supplied. For example, second supply flow channel 402 may have a pump for supplying the sample solution. The other end of second supply flow channel 402 corresponds to analyte supply port 309.

From the other end of third supply flow channel 403, second oil 408 is supplied. For example, third supply flow channel 403 may have a pump for supplying second oil 408. The other end of third supply flow channel 403 corresponds to oil supply port 311.

One end of the fourth flow channel corresponds to junction 411. From first supply flow channel 401, second supply flow channel 402, and third supply flow channel 403, respective liquids flow at respective constant flow rates, and the liquids converge (collide) at junction 404 of flow channels. As aqueous sample solution 407 and reaction chemical solution 405, and first oil 406 and second oil 408 converge at junction 404 of flow channels, aqueous sample solution 407 and reaction chemical solution 405 are torn off by first oil 406 and second oil 408, and thus drop 409 is generated. The size of drop 409 is determined by the discharge ratio between the aqueous solutions (e.g., sample solution 407 and reaction chemical solution 405) and oils 406, 408 at junction 404 of flow channels. The larger the proportion of discharge of aqueous solutions 405, 407 to oils 406, 408, the larger the size of generated drop 409 becomes.

From first supply flow channel 401, aqueous reaction chemical solution 405 and first oil 406 flow alternately. The generation condition of drop 409 differs between the case where reaction chemical solution 405 reaches junction 404 of flow channels and the case where first oil 406 reaches junction 404 of flow channels. FIG. 4A shows the state that reaction chemical solution 405 has reached junction 404 of flow channels. At junction 404 of flow channels, aqueous reaction chemical solution 405 flowing from first supply flow channel 401, aqueous sample solution 407 flowing from second supply flow channel 402, and second oil 408 flowing from third supply flow channel 403 converge. In this case, the mixture of aqueous sample solution 407 and reaction chemical solution 405 is torn by second oil 408, and as shown in FIG. 4A, drops 409 in which sample solution 407 and reaction chemical solution 405 are mixed are generated with second oil 408 interposed between the drops, and thus a group of drops is formed.

FIG. 4B shows the state that first oil 406 has reached junction 404 of flow channels from first supply flow channel 401. At junction 404 of flow channels, first oil 406 flowing from first supply flow channel 401, aqueous sample solution 407 flowing from second supply flow channel 402, and second oil 408 flowing from third supply flow channel 403 converge. In this case, aqueous sample solution 407 is torn by first oil 406 flowing from first supply flow channel 401, and by second oil 408 flowing from third supply flow channel 403, and as shown in FIG. 4B, drops 410 composed exclusively of sample solution 407 are generated with the mixture of the first oil and the second oil interposed between the drops, and thus a group of drops is formed.

Since respective liquids flow from first supply flow channel 401, second supply flow channel 402, and third supply flow channel 403 while keeping respective constant flow rates, in the state that reaction chemical solution 405 from first supply flow channel 401 has reached junction 404 of flow channels as shown in FIG. 4A, the proportion of the discharge of the aqueous solution to the discharge of the oil at the time of generation of a drop is larger compared with the state that first oil 406 from first supply flow channel 401 has reached junction 404 of flow channels as shown in FIG. 4B, and thus the size of the generated drop is larger. In other words, when the chemical solution tank (reaction chemical solution library) as shown in FIG. 2 is formed, and the respective liquids are flown to the flow channel converging part as shown in FIG. 4 at respective constant flow rates, a group of drops 409 containing a reaction chemical solution, and a group of drops 410 not containing a reaction chemical solution are alternately generated, and the size of drop 409 containing a reaction chemical solution is larger than the size of drop 410 not containing a reaction chemical solution.

In the state that reaction chemical solution 405 from first supply flow channel 401 has reached junction 404 of flow channels as shown in FIG. 4A, the proportion of the discharge of the aqueous solution to the discharge of oil is larger in comparison with the state that first oil 406 from first supply flow channel 401 has reached junction 404 of flow channels as shown in FIG. 4B, so that the size of the generated drop is larger, and inversely the amount of oil between drops is smaller. This owes to the quantitative balance between the aqueous solution and oil at the time of generation of a drop at junction 404 of flow channels. In other words, in the group of drops 409 containing reaction chemical solution 405 generated in the condition of FIG. 4A, the amount of oil between drops is smaller in comparison with the group of drops 410 not containing reaction chemical solution 405 generated in the condition of FIG. 4B. That is, the size of the oil part is smaller.

These are determined by the balance between the discharge of the aqueous solution and the discharge of the oil at the time of generation of a drop at junction 404 of flow channels, and as shown in FIGS. 4A and 4B, and by configuring the reaction chemical solution library that allows the reaction chemical solution and the oil to flow alternately from first supply flow channel 401 in the flow channel converging part which is a junction of first supply flow channel 401, second supply flow channel 402, and third supply flow channel 403, the size of drop 409 containing reaction chemical solution 405 is necessarily larger than the size of drop 410 not containing reaction chemical solution 405 by setting the respective flow rates of the liquids flowing from the respective supply channels constant even if the discharge of liquid from each supply flow channel is set differentially. Also, the size of oil in the group of drops 409 containing reaction chemical solution 405 is smaller than the size of oil in the group of drops 410 not containing reaction chemical solution 405.

While the flow channel configuration shown in FIGS. 4A and 4B has been described, the way of junction of flow channels is not limited to the form shown in these drawings, and any way of junction can be employed. For example, the first supply flow channel, the second supply flow channel, and the third supply flow channel may be connected at 90 degrees one another, namely they may be connected in the shape of a cross. Changing the way of junction will not influence on the effect as long as the respective liquids are supplied from the first supply flow channel, the second supply flow channel, and the third supply flow channel at respective constant flow rates.

Figure 5:
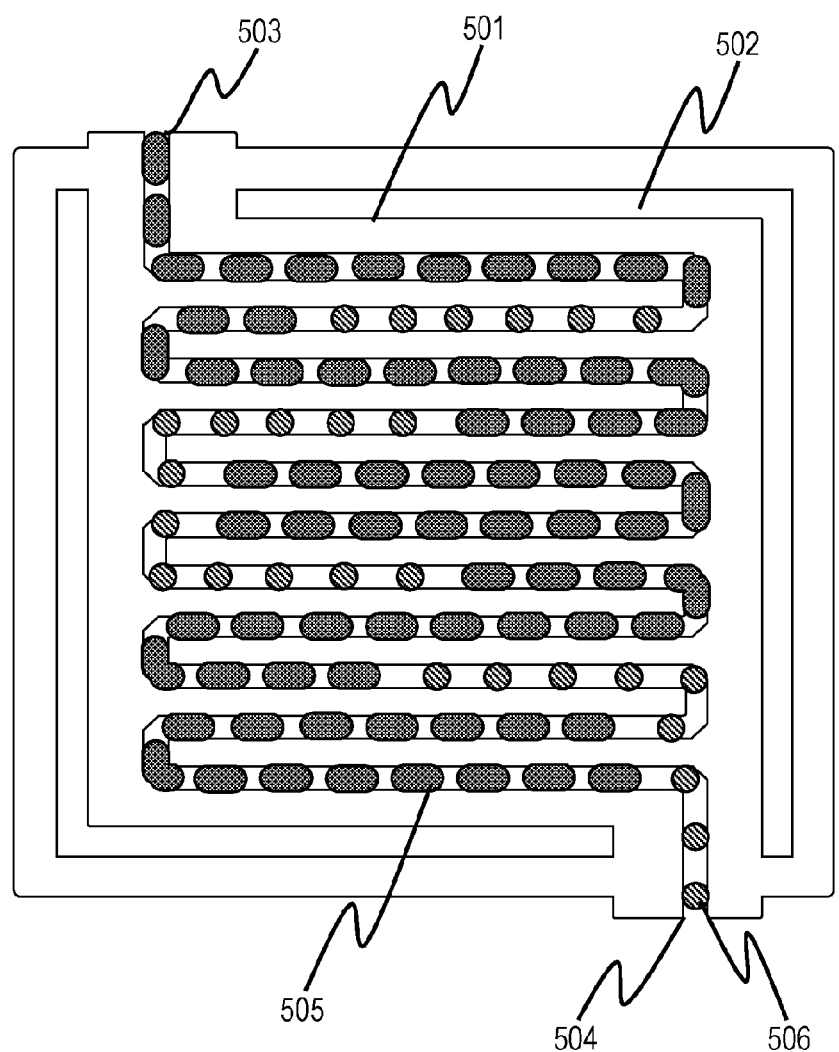
FIG. 5 is a schematic diagram showing one exemplary constitution of a PCR reactor.

FIG. 5 is a schematic diagram showing one exemplary constitution of a PCR (polymerase chain reaction) reactor for amplifying nucleic acid targets. Also in the PCR reactor, it is necessary for the group of drops generated in the flow channel converging part to flow without disturbance of the order of generation. Therefore, also in the PCR reactor, one flow channel runs continuously as shown in FIG. 5, and drops sequentially flow one by one without change of the order. In the PCR reactor, a nucleic acid amplification treatment by PCR is conducted.

Figure 6A:
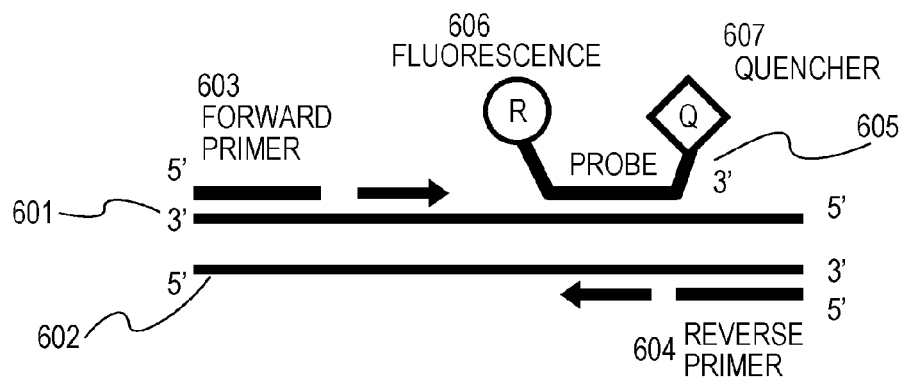
FIG. 6A is a schematic diagram showing each process in PCR using a TaqMan probe.
Figure 6B:
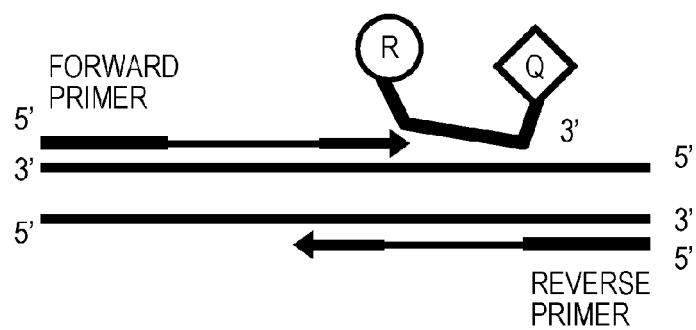
FIG. 6B is a schematic diagram showing each process in PCR using the TaqMan probe.
Figure 6C:
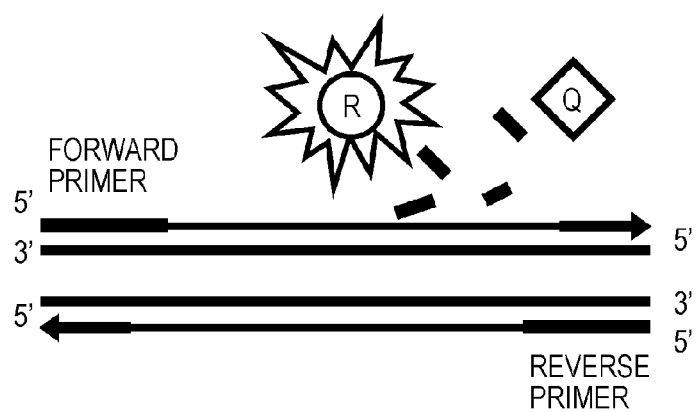
FIG. 6C is a schematic diagram showing each process in PCR using the TaqMan probe.

As one example of the PCR (polymerase chain reaction), FIGS. 6A to C are diagrams showing each process of the nucleic acid amplification treatment by PCR using a fluorescent probe called TaqMan probe. An analyte such as blood or body fluid is preliminarily treated by a pretreatment means shown in FIG. 3B so that the nucleic acid amplification treatment by PCR can be conducted. Examples of the treatment include destroying cells, destroying endoplasmic reticula such as exosome contained in blood or body fluid, concentrating nucleic acid contained therein at high concentration by a technique such as filtering and so on. In order to conduct the nucleic acid amplification treatment by PCR, it is necessary to make the nucleic acid have a double-stranded structure having a base sequence of a certain degree of length (a base sequence that is sufficiently longer than at least the primer and the probe in the reaction chemical solution) after conducting the aforementioned treatment. For example, when a very short nucleic acid fragment of about 20 base pairs such as miRNA is set as a nucleic acid target, a treatment for converting miRNA into longer double-stranded DNA, which is called reverse transcription, is required. Such a treatment is also included in the pretreatment means. The method of the pretreatment step does not influence on the effect, and any method can be employed.

As shown in FIG. 6A, nucleic acid having reached in the PCR reactor has a double-stranded structure of complementarily aligned base sequences (the state in which 601, 602 are bound). As the nucleic acid is heated to a certain temperature, the double strand is dissociated, and separated into single-stranded nucleic acids (601, 602). For the sample of single-stranded nucleic acids, if single-stranded nucleic acid 601 is a nucleic acid target to be detected, for example, primer (603) having a sequence that is complementary to a first region of the sequence chain of nucleic acid targets 601, and a fluorescent probe including a sequence that is complementary to a second region of the sequence chain of the same nucleic acid target (oligonucleotide labeled with a fluorescent dye, 605) are brought into contact with the sample, and they are brought into the condition that causes hybridization. As a result, primer 603 and fluorescent probe 605 form a double-stranded complex together with nucleic acid target 601 (see FIG. 6A). Also to single-stranded DNA 602 which is not a nucleic acid target, corresponding primer 604 binds. However, since single-stranded DNA 602 is not a nucleic acid target to be detected, fluorescent probe 605 does not bind thereto.

Then the condition is varied to enable 5'→3' nuclease activity, and thus a nucleic acid synthase starts working, and elongation of nucleic acid starts from primers 603, 604 bound to single-stranded nucleic acids 601 and 602 as origins (see FIG. 6B).

As the elongation of the nucleic acid advances, fluorescent probe 605 bound to nucleic acid target 601 is liberated (see FIG. 6C). Fluorescent dye 606 and quencher 607 included in fluorescent probe 605 do not cause lighting of the fluorescent dye before liberation because they are present in close regions. However, when the fluorescent probe is liberated, and fluorescent dye 606 and quencher 607 are separated from each other as a result of the elongation of the nucleic acid, fluorescence can be developed. Through this cycle of sequence, one fluorescent dye is liberated per one nucleic acid target, and light emission is possible. Since each single-stranded nucleic acid turns into double-stranded nucleic acid as a result of the elongation of the nucleic acid, the nucleic acid is amplified double. In brief, by repeating this process, the number of nucleic acid is amplified $2^n$ (n is the number of repetition of the process) times depending on the number of repetition, and similarly, liberation of the fluorescent dye occurs $2^n$ times. When the nucleic acid target to be detected is contained in the sample, the quantity of the fluorescent dye capable of emitting light increases as the process is repeated.

Although the condition differs depending on the kinds of the primer and the fluorescent probe, heating is typically conducted at a temperature around 90° C. to separate double-stranded nucleic acid into single-stranded nucleic acid, at a temperature around 60° C. to allow hybridization of a primer and a fluorescent probe, and at a temperature around 70° C. to enable the nuclease activity and make the nucleic acid synthase function to elongate nucleic acid. That is, the nucleic acid amplification treatment by PCR is carried out by conducting a temperature cycle in which heating and cooling are repeated at temperatures ranging from around 90° C. to around 60° C. Since the PCR reactor needs to repeat the temperature cycle at high speed, when a material excellent in thermal conductivity such as a Si substrate is used as a substrate as in the first exemplary embodiment, for example, thermal insulating measure such as separating the region of the reactor where the temperature cycle is to be conducted, from the Si member is useful. Also in the first exemplary embodiment, around reactor 501 of the PCR reactor formed on the Si substrate in FIG. 5, clearance (gap) 502 is formed by the method such as etching. With this constitution, the heat for heating the reactor will not diffuse circumferentially, and a very high-speed temperature cycle can be realized. Further, for making it possible to change the temperature of the entire PCR reactor to conduct the amplification treatment of nucleic acid target by PCR on the whole drops in the reactor, a temperature control device such as a Peltier element may be brought into contact in such a manner that it cover the entire PCR reactor. Alternatively, a metal plate of Cu or Al having high thermal conductivity may be brought into contact with a Peltier element, and the metal plate may be brought into contact with the entire PCR reactor.

In the PCR reactor, a group of drops generated in the flow channel converging part of the previous stage sequentially flow in the same order as they are generated through supply port 503. In conducting PCR, for example, supply port 503 of the PCR reactor, and a valve provided near outlet 504 are closed so as to retain the group of drops within reactor 501.

In drop 505 containing a reaction chemical solution, a sample solution containing nucleic acid, and a reaction chemical solution of a primer, a probe, an enzyme and the like are contained. The shape of drop (505 or 506) in the PCR reactor will not be destroyed by the temperature cycle of PCR. That is, in each drop, the nucleic acid amplification treatment by PCR is conducted individually. In the case where a nucleic acid target to be detected is contained in a drop, nucleic acid is amplified in the drop, and the quantity of the liberated fluorescent dye increases with the number of temperature cycles. That is, when a drop is irradiated with light of the wavelength that excites fluorescence, the drop develops fluorescence. In the case where a nucleic acid target to be detected is not contained in a drop, the fluorescent dye will not be liberated even if the nucleic acid amplification treatment by PCR is conducted, and the drop will not develop fluorescence even if it is irradiated with light of the wavelength that excites fluorescence. That is, by counting the proportion of the number of drops developing fluorescence to the total number of the group of drops containing the same kind of reaction chemical solution, it is possible to analyze the degree of proportion of the nucleic acid target to be detected contained in the original sample.

While the PCR reactor having the shape shown in FIG. 5 has been described, any constitution other than the shape shown in FIG. 5 will not influence on the effect as long as the drops can sequentially flow one by one in the same order as they are generated, and the temperature cycle of PCR can be realized for the entire region in the PCR reactor.

Figure 7:
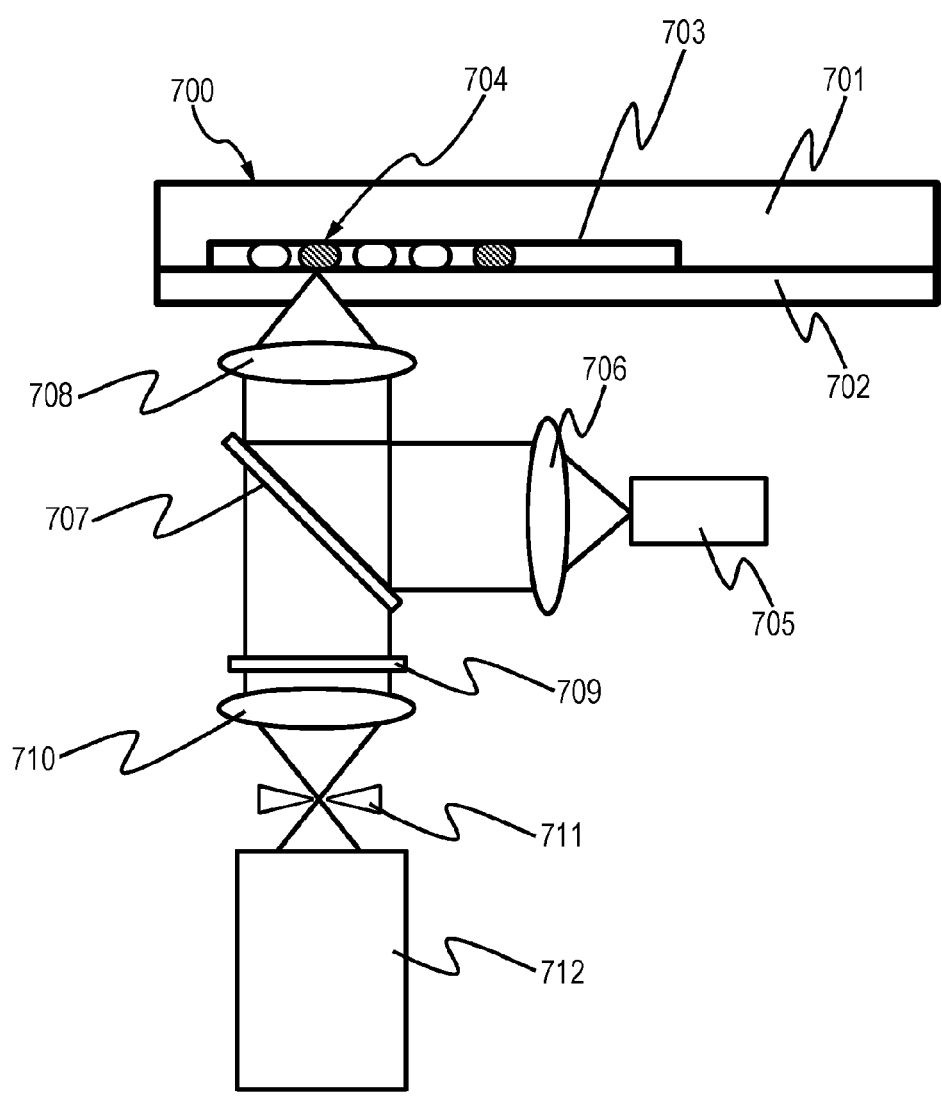
FIG. 7 is a schematic diagram showing one exemplary constitution of an optical waveguide of a microfluidic chip and an optical system of a nucleic acid target analyzer in the first exemplary embodiment.

FIG. 7 is a schematic diagram showing one exemplary constitution of an optical waveguide of microfluidic chip 700 and an optical system of a nucleic acid target analyzer in the first exemplary embodiment.

The optical waveguide of microfluidic chip 700 is configured by forming a groove of several hundred micrometers on a base material such as Si substrate 701, and bonding glass plate 702 thereon by a method of anode bonding or the like. The groove is bonded with glass plate 702, and thus it becomes flow channel 703 through which a drop flows. In flow channel 703 formed of the groove, drops 704 after PCR flow continuously in line at a predetermined constant speed. It is necessary to irradiate drop 704 with light that excites the fluorescent dye, and to detect the fluorescence emitted by the irradiation. In the chip of this constitution, input/output of light is conducted through the glass surface. Flow channel 703 in which drops after amplification in the PCR reactor flow is also referred to as the fifth flow channel.

As the light source, often used is laser, LED or the like having a wavelength near the maximum absorption wavelength of the absorption spectrum of the fluorescent dye so as to excite the fluorescent dye efficiently. In particular, the optical system preferably has the least possible size and the highest possible output, and as the light source, a semiconductor laser or the like is preferred. In the first exemplary embodiment, for example, semiconductor laser 705 having a wavelength of 650 nm is used.

Laser light emitted from semiconductor laser 705 is collimated by collimator lens 706, and reflected by dichroic mirror 707. A dichroic mirror is a mirror capable of selecting reflection or transmission depending on the wavelength, and in the first exemplary embodiment, a dichroic mirror having a cutoff of 660 nm is used. The light having a wavelength shorter than 660 nm is reflected, and the light having a wavelength longer than 660 nm is transmitted.

The reflected laser light is condensed at a drop passage position in fifth flow channel 703 by object lens 708. Since drop 704 containing a nucleic acid target is in such a state that a large quantity of the fluorescent dye is liberated in the drop by PCR, the fluorescent dye is excited by the laser irradiation to emit fluorescence. Part of the fluorescence emitted from drop 704 is taken out on the side of the fluorescent detector through object lens 708. Since object lens 708 is required to take in the fluorescence as efficiently as possible, a lens having a large numerical aperture (NA) is preferred. In the first exemplary embodiment, an object lens having an NA of 0.85 is used. The fluorescence having passed through object lens 708 passes through dichroic mirror 707. Then after controlling the intensity of the light other than fluorescence (for example, leakage of excitation light, and autofluorescence emitted from other material) through optical filter 709 that transmits only the light of fluorescent wavelength, the light is condensed in the fluorescent detector by lens 710. By providing the point condensed by the lens with pinhole 711 having such a size that exactly transmits the condensed light, it becomes possible to cut a stray light component in the laser light concentrated in the sensor chip reflected from the region other than the focus. Only the fluorescence having penetrated the pinhole is inputted to fluorescent detector 712.

Since the fluorescent detector is required to detect fluorescence generally having a magnitude of ten-thousandth to a hundred-thousandth of excitation light with high sensitivity and at high speed, a high-sensitive detector such as a photomultiplier (PMT), an avalanche photodiode (APD), or a photodiode (PD) is used. In particular, PMT which is excellent in sensitivity and high in response speed is preferred. In the first exemplary embodiment, a current-output type PMT is used.

By a boundary detector, boundaries between the first drops to the fourth drops flowing in the fifth flow channel are acquired according to the intensity of fluorescence. The detector acquires numbers of the second drops and the fourth drops having an intensity of fluorescence greater than or equal to a first threshold, based on the intensity of fluorescence, and boundaries between the first drops to the fourth drops, and detects whether or not at least one selected from the group consisting of a first nucleic acid target and a second nucleic acid target is contained in the objective nucleic acid targets based on the numbers of the second drops and the fourth drops.

In the present disclosure, the boundary detector and the detector may be implemented by one or more than one electronic circuit including a semiconductor device, a semiconductor integrated circuit (IC), or a LSI (large scale integration). LSI or IC may be integrated in one chip, or may be configured by combination of a plurality of chips. For example, a functional block other than a memory element may be integrated in one chip. While the designations of LSI and IC are used herein, the designation varies depending on the degree of integration, and they may be designated as system LSI, VLSI (very large scale integration), or ULSI (ultra large scale integration). Field Programmable Gate Array (FPGA) that is programmed after production of LSI, or a reconfigurable logic device that allows reconstitution of a joint relation inside LSI or setup of circuit section inside LSI can also be used for the same purpose.

<Method for Analyzing Multiple Nucleic Acid Targets>

Hereinafter, a method for analyzing multiple nucleic acid targets by separating and detecting a group of drops containing different multiple reaction chemical solutions will be described.

As already described with reference to FIGS. 4A and 4B, in the flow channel converging part, a group of drops containing a reaction chemical solution and a group of drops not containing a reaction chemical solution are alternately generated. The size of a drop containing a reaction chemical solution is necessarily larger than the size of a drop not containing a reaction chemical solution. The drops generated in the flow channel converging part flow in one thin flow channel through the PCR reactor without disturbance of the order of generation, and sequentially pass by the drop passage position in the flow channel of the optical waveguide.

The upper stage of FIG. 1 is a schematic diagram showing a plurality of groups of drops flowing in one flow channel of an optical waveguide of a microfluidic chip, and the lower stage of FIG. 1 shows one example of an output signal measured for the plurality of groups of drops shown in the upper stage of FIG. 1. That is, the upper stage of FIG. 1 shows the state of drops near a drop passage position in a fifth flow channel of an optical waveguide. As shown in the upper stage of FIG. 1, a group of drops containing a reaction chemical solution 101 or 102, and a group of drops not containing a reaction chemical solution 103 or 104 appear alternately. The upper stage of FIG. 1 illustrates the appearance in which the group of drops not containing a reaction chemical solution 103, the group of drops containing a reaction chemical solution 101, the group of drops not containing a reaction chemical solution 104, and the group of drops containing a reaction chemical solution 102 flow sequentially. One point in the fifth flow channel is defined as a drop passage position, and the fixed point is irradiated with fluorescence excitation light concentrated by the object lens. Due to a difference in refractive index between drop and oil, the intensity of reflected light near the fluorescent wavelength taken in through the objective lens changes in the boundary part between the drop and the oil. In other words, by irradiating the drop passage position with fluorescence excitation light that is concentrated into the size equivalent, or preferably smaller than the size of the drop by means of the object lens, a change in intensity of signal as illustrated in the lower stage of FIG. 1 appears every time a drop passes by the drop passage position in the fluorescent detector (for example, current output of PMT). Since the drops flow while keeping constant flow rates, the crossing time at the time of crossing the drop passage position varies depending on the size of the drop. For example, by providing a threshold for the output level of the fluorescent detector, and acquiring information of the position where threshold 110 and a signal intersect, it is possible to measure crossing time (112, 113) of each one of the drops. A drop containing a reaction chemical solution, which is larger in size, takes a longer crossing time compared with a drop not containing a reaction chemical solution. That is, while drops containing a reaction chemical solution are flowing at the drop passage position, relatively long pulsed signal patterns 107, 108 continue for the duration corresponding to the number of drops. Then, drops not containing a reaction chemical solution are flown to the drop passage position, and shorter pulsed signal pattern 109 continues for the duration corresponding to the number of drops. By preliminarily measuring the crossing time of a drop, it is possible to determine a boundary between a longer pulsed signal and a shorter pulsed signal. The foregoing process is conducted by the boundary detector. In brief, the boundary detector acquires boundaries between the first drops to the fourth drops flowing in the flow channel of the fifth flow channel based on the intensity of fluorescence.

In the group of drops containing a reaction chemical solution, a drop containing a nucleic acid target to be detected is occasionally contained. A drop containing a nucleic acid target to be detected is in such a state that a large number of fluorescent dye molecules are liberated by the nucleic acid amplification treatment in the PCR reactor, and the fluorescent dye is excited by the radiation of fluorescence excitation light, and fluorescence is emitted from the drop. That is, in the group of drops, only weak signal 108 is detected from a drop not containing a nucleic acid target, and larger signal 107 is detected from a drop containing a nucleic acid target. By separating the intensity of the output signal of the fluorescent detector according to whether or not it exceeds a certain threshold, it is possible to determine the proportion of the number of drops emitting fluorescence to the total number of drops in the group of drops containing a reaction chemical solution by calculation. In the lower stage of FIG. 1, when a signal exceeding threshold 111 is detected, the drop is determined as a fluorescent drop containing a nucleic acid target. In other words, by counting the number of drops exceeding threshold 110, the total number of drops is determined, and by counting the number of drops exceeding threshold 111, the number of fluorescent drops, namely drops containing a nucleic acid target is determined. The foregoing process is conducted by the detector. In other words, the detector acquires the numbers of the second drops and the fourth drops having intensity of fluorescence exceeding the first threshold based on the intensity of fluorescence, and the boundaries between the first drops to the fourth drops, and detects whether or not the objective nucleic acid target contains at least one selected from the group consisting of the first nucleic acid target and the second nucleic acid target based on the numbers of the second drops and the fourth drops.

Regarding the case where the reaction chemical solution library shown in FIG. 2 is used, the optical waveguide and the processing method in the method for analyzing multiple nucleic acid targets will be described.

First, a group of drops with a large size (taking a long crossing time) containing reaction chemical solution A flows. Assuming that 100 drops containing reaction chemical solution A flow continuously, the output signal of the fluorescent detector fluctuates in the optical waveguide every time the drop passes by as shown in the lower stage of FIG. 1. By comparing the fluctuating signal with certain first threshold 110, and counting the number of times of crossing first threshold 110, the number of drops can be grasped. Since 100 drops flow, the pulsed signal continuously appears 100 times. Then a group of drops with a small size (taking a short crossing time) not containing a reaction chemical solution flows. Assuming that 50 drops not containing a reaction chemical solution flow continuously, the length (crossing time) of the pulsed signal detected in the fluorescent detector changes in the boundary part between the group of drops containing reaction chemical solution A and the group of drops not containing a reaction chemical solution. It is therefore possible to determine that the group of drops containing reaction chemical solution A ends at the 100th drops by monitoring the length of the signal. The 100 drops containing reaction chemical solution A include some drops in which the intensity of fluorescence is strongly detected, and the number of the drops is now assumed ten. When the ten drops pass by the drop passage position, a very strong signal is detected in comparison with the output signal of the fluorescent detector when other drop flows. By comparing it with second threshold 111 which is stronger in intensity than first threshold 110, it is possible to detect the number of drops in which intensity of fluorescence is strongly detected. That is, in the case of this example, it is revealed that the number of nucleic acid targets that react with reaction chemical solution A in one-to-one correspondence is only ten among the total of 100 drops containing reaction chemical solution A. From the proportion of the number of fluorescent drops to the total number of drops, it is possible to calculate the degree of proportion of the nucleic acid targets that react with reaction chemical solution A in one-to-one correspondence contained in the original sample solution.

The sample solution is diluted, and the concentration thereof is adjusted so that about one nucleic acid molecule is contained in one drop, however, it is not necessary that one nucleic acid molecule is contained in one drop. For example, some drops may not contain a nucleic acid molecule, or some drops contain two nucleic acid molecules. However, this can be processed stochastically, and can be estimated according to the idea of Poisson distribution. By adapting the idea of Poisson distribution, an average value of the number of nucleic acid molecules contained in a drop is determined from the proportion of fluorescent drops to the total number of drops. In the case where the proportion of fluorescent drops to the total number of drops is defined as p, the average of the number of nucleic acid molecules contained in a drop can be determined by the numerical formula $-\ln(1-p)$. For example, in the previous example, since the number of fluorescent drops is ten with respect to the total number of drops of 100, the proportion of fluorescent drops to the total number of drops is 0.1. Since the average of the number of nucleic acid molecules contained in one drop is 0.11 from the idea of Poisson distribution, it can be estimated that 11 nucleic acid target molecules are contained in the sample solution of the volume corresponding to the total of 100 drops. If the number of drops and the number of fluorescent drops can be counted while the group of drops formed of the same kind of reaction chemical solution are clearly discriminated from the group of drops formed of other reaction chemical solution as described above, the quantity of the nucleic acid targets contained in the sample solution can be analyzed quantitatively.

After 50 drops not containing a reaction chemical solution flow, a group of drops with a large size (taking a long crossing time) containing reaction chemical solution B flows. Since the length (crossing time) of the pulsed signal detected by the fluorescent detector changes in the boundary part between the group of drops not containing a reaction chemical solution and the group of drops containing reaction chemical solution B, it is possible to confirm the position of the first drop in the group of drops containing reaction chemical solution B by monitoring the length of the signal. Also for the group of drops containing reaction chemical solution B, it is possible to calculate the degree of proportion of the nucleic acid targets that react with reaction chemical solution B in one-to-one correspondence contained in the original sample solution by counting the total number of drops containing reaction chemical solution B and the number of fluorescent drops exceeding the second threshold in the same manner as conducted for the group of drops containing reaction chemical solution A.

From then on, the procedure as described above is repeated. When ten kinds of reaction chemical solutions (reaction chemical solutions A to J) are stored in the chemical solution tank as shown in FIG. 2, the repetition of the group of drops containing a reaction chemical solution and the group of drops not containing a reaction chemical solution occur ten times. Since the start and end of the group of drops containing a reaction chemical solution can be grasped by confirming the change in length (crossing time) of the pulsed signal detected by the fluorescent detector, the ten kinds of nucleic acid targets can be analyzed sequentially by counting the number of fluorescent drops with respect to the number of drops for each reaction chemical solution.

In the first exemplary embodiment, for example, the same material is used as the first oil and the second oil. The first oil and the second oil are not necessarily the same material as long as the first oil and the second oil can clearly separate the aqueous solution; however, when the first oil and the second oil are mixed in the flow channel converging part, the stability of the chemical solution during mixing and the drop generation condition will not change by forming the first oil and the second oil of the same material. Therefore, it is more preferred to use the same material as the first oil and the second oil.

Also in the first exemplary embodiment, for example, an identical one fluorescent dye is used as the fluorescent dyes contained in different multiple reaction chemical solutions. The fluorescent dyes are not necessarily the identical one fluorescent dye, but a greater effect is obtained by using a fluorescent dye which emits fluorescence having the same wavelength for all the reaction chemical solutions because the constitutions of the optical waveguide and the optical system of the multiple nucleic acid target analyzer can be very simple.

Figure 8:
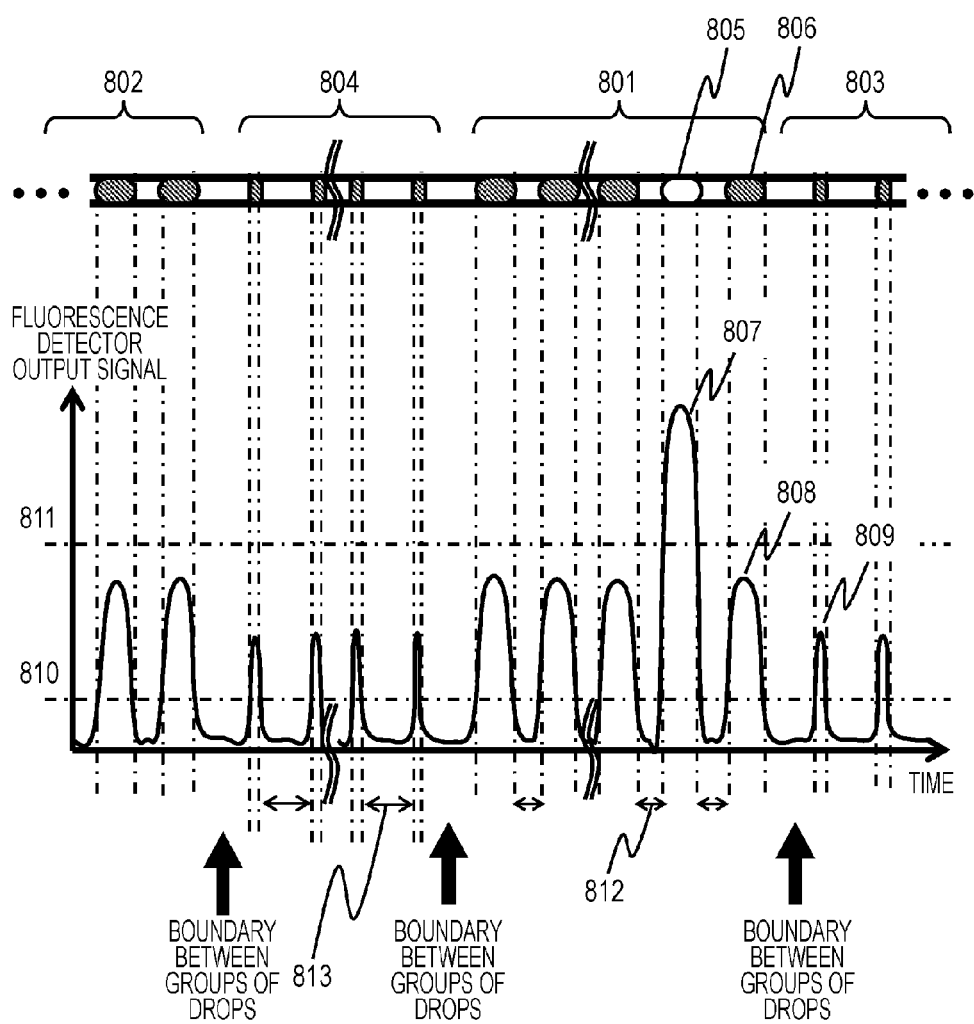
FIG. 8 includes a schematic diagram showing a plurality of groups of drops flowing in one flow channel of an optical waveguide of a microfluidic chip (upper stage) and one example of an output signal measured for the plurality of groups of drops (lower stage)

In the lower stage of FIG. 1, boundaries between groups of drops containing a reaction chemical solution 101, 102, and groups of drops not containing a reaction chemical solution 103, 104 are determined according to the information of the size of drop (crossing time of drop) 112, 113. Not limited to this, for example, as shown in the upper stage and the lower stage of FIG. 8, boundaries can also be determined by measuring crossing time 812 of oil in groups of drops containing a reaction chemical solution 801, 802, and crossing time 813 of oil in groups of drops not containing a reaction chemical solution 803, 804. Similarly to FIG. 1, FIG. 8 shows a signal pattern detected by the optical waveguide, and illustration of a method for separating and detecting a group of drops containing different multiple reaction chemical solutions. As illustrated by referring to FIG. 4, groups of drops containing a reaction chemical solution 801, 802, and groups of drops not containing a reaction chemical solution 803, 804 are alternately generated in the flow channel converging part. The size of oil part in groups of drops containing a reaction chemical solution 801, 802 is necessarily smaller than the size of oil part in groups of drops not containing a reaction chemical solution 803, 804. The drops generated in the flow channel converging part flow in one thin flow channel through the PCR reactor without disturbance of the order of generation, and sequentially pass by the drop passage position in the flow channel of the optical waveguide. The upper stage of FIG. 8 shows the state of drops near the drop passage position in the flow channel of the optical waveguide. As shown in the upper stage of FIG. 8, a group of drops containing a reaction chemical solution 801 or 802, and a group of drops not containing a reaction chemical solution 803 or 804 appear alternately. The upper stage of FIG. 8 illustrates the appearance in which the group of drops not containing a reaction chemical solution 803, the group of drops containing a reaction chemical solution 801, the group of drops not containing a reaction chemical solution 804, and the group of drops containing a reaction chemical solution 802 flow sequentially. Similarly to the above, the crossing time of oil part in the group of drops differs between the group of drops containing a reaction chemical solution and the group of drops not containing a reaction chemical solution. It is therefore possible to grasp the start and end of the group of drops containing a reaction chemical solution based on the information. By separating the groups of drops depending on the kind of the reaction chemical solution based on the information, and counting the number of fluorescent drops exceeding the second threshold with respect to the total number of group of drops containing the same kind of reaction chemical solution, it is possible to calculate the degree of proportion of the nucleic acid targets contained in the original sample solution.

Second Exemplary Embodiment

A second exemplary embodiment of the present disclosure differs from the first exemplary embodiment only in the structure of the flow channel converging part where a drop is generated. Other constitution is the same as the constitution of the first exemplary embodiment, and therefore description will be omitted.

Figure 9A:
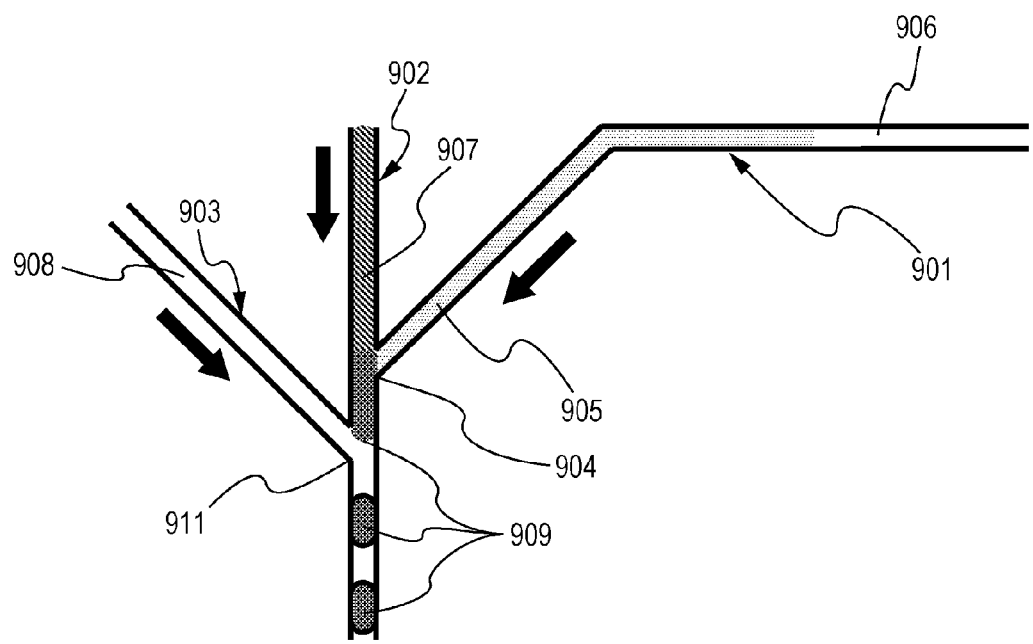
FIG. 9A is a schematic diagram showing one exemplary constitution of a flow channel converging part in a second exemplary embodiment.
Figure 9B:
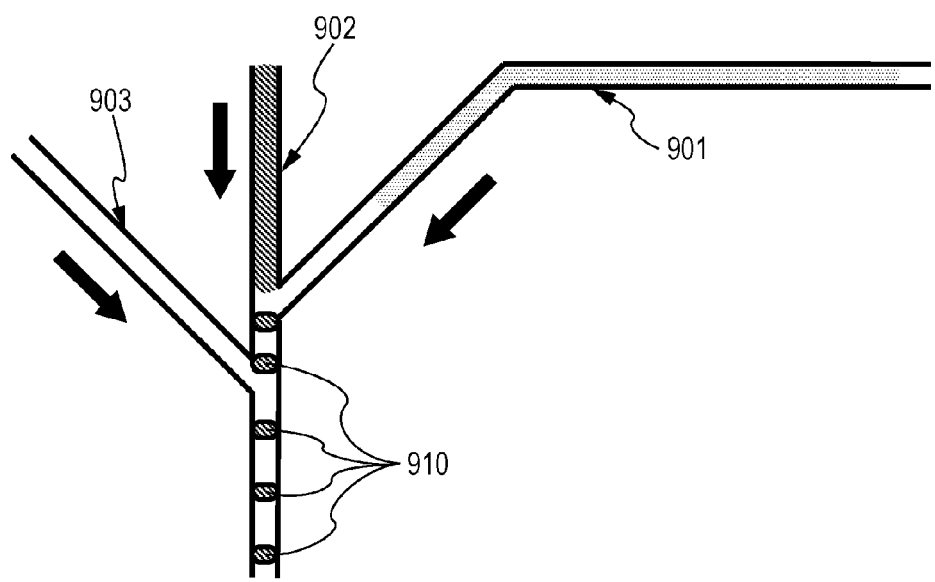
FIG. 9B is a schematic diagram showing one exemplary constitution of the flow channel converging part in the second exemplary embodiment.

FIG. 9A is a schematic diagram showing one exemplary constitution of the flow channel converging part in the second exemplary embodiment, and shows the state that a reaction chemical solution flows into junction 904 from the first supply flow channel, and FIG. 9B shows the state that the first oil flows into junction 904 from the first supply flow channel.

As shown in the drawings, in the flow channel converging part where a drop is generated in the second exemplary embodiment, first supply flow channel 901 connecting from the outlet of the chemical solution tank shown in FIG. 2, through which multiple reaction chemical solutions and the first oil flow alternately, and second supply flow channel 902 connecting from the pretreatment means that prepares a sample solution containing nucleic acid that is to be examined from an analyte such as blood or body fluid, through which a sample solution containing nucleic acid flows are connected at junction 904. The connected flow channel and third supply flow channel 903 through which the second oil flows are connected at junction 911. From the first supply flow channel, the second supply flow channel, and the third supply flow channel, respective liquids flow at respective constant flow rates, and the liquids converge at junction 904, and junction 911 of flow channels. When aqueous sample solution 907 or reaction chemical solution 905, and oil 906, 908 converge at a junction of flow channels, aqueous sample solution 907 or reaction chemical solution 905 is torn by the oil, and drop 909 is generated. The size of drop 909 is determined by the discharge ratio between the aqueous solution (for example, the sample solution or the reaction chemical solution) and the oil at the junction of flow channels. The larger the proportion of the discharge of the aqueous solution to the discharge of the oil, the larger the size of generated drop becomes.

From first supply flow channel 901, aqueous reaction chemical solution 905 and first oil 906 flow alternatively. The generation condition of drop differs between the case where reaction chemical solution 905 reaches junction 904 of flow channels and the case where first oil 906 reaches junction 904 of flow channels. FIG. 9A shows the state that reaction chemical solution 905 has reached junction 904 of flow channels. At junction 904 of flow channels, aqueous reaction chemical solution 905 flowing from first supply flow channel 901, and aqueous sample solution 907 flowing from second supply flow channel 902 converge. Since both solutions are aqueous solutions, they flow toward next junction 911 while mingling together. They join second oil 908 flowing from third supply flow channel 903 at junction 911. At junction 911, the mixture of reaction chemical solution 905 and sample solution 907 is torn by second oil 908, and a group of drops 909 in which the sample solution and the reaction chemical solution are mixed are generated with second oil 908 interposed between drops as shown in the drawing.

FIG. 9B shows the state that first oil 906 has reached junction 904 of flow channels from first supply flow channel 901. At junction 904 of flow channels, first oil 906 flowing from first supply flow channel 901, and aqueous sample solution 907 flowing from second supply flow channel 902 converge. In this case, aqueous sample solution 907 is torn by first oil 906 flowing from first supply flow channel 901, and a group of drops 910 composed exclusively of the sample solution are formed with first oil 906 interposed between drops as shown in the drawing. Then aqueous sample solution 907 joins second oil 908 flowing from third supply flow channel 903 at junction 911, and sample solution 907 that has already become small drops 910 flows in the condition that intervals between drops are extended by mixed oil of the first oil and the second oil without being torn by second oil 908 flowing from third supply flow channel 903. As shown in the drawing, the group of drops 910 formed exclusively of the sample solution is generated with the mixture of the first oil and the second oil interposed between drops.

From first supply flow channel 901, second supply flow channel 902, and third supply flow channel 903, the respective liquids flow while keeping the respective constant flow rates. The setting of discharge of each liquid flowing from each supply flow channel is typically made in the ratio as described below. For amplifying a nucleic acid target in the later nucleic acid amplification treatment, generally, a large quantity of reaction chemical solution (primer, probe, enzyme and so on) is required for the sample solution containing nucleic acid, and a large discharge is set for second supply flow channel 902 from first supply flow channel 901. For example, it may be set, for example, about 10 times to 15 times. Also it may be set so that the second oil of the discharge equivalent to the mixed solution mixed at junction 904 is supplied from the third supply flow channel to stabilize generation of drops. That is, if discharge per unit time of sample solution 907 flowing from second supply flow channel 902 is 1, reaction chemical solution 905 or first oil 906 having discharge 15 flows from first supply flow channel 901, and second oil 908 having discharge 16 flows from third supply flow channel 903. As just mentioned, it is generally assumed that discharges of the reaction chemical solution, the first oil, and the second oil are set large relative to the sample solution. As shown in FIG. 9A, in the state that reaction chemical solution 905 has reached junction 904 of flow channels from first supply flow channel 901, and the mixed solution has reached junction 911, the discharge ratio between the mixed solution and the second oil is approximately 1:1. Considering the fact that the discharge ratio between the sample solution and the first oil at junction 904 of flow channels is 1:15 in the state that first oil 906 has reached junction 904 of flow channels from first supply flow channel 901 as shown in FIG. 9B, the size of each drop is larger in the group of drops 909 than in the group of drops 910. That is, when the chemical solution tank (reaction chemical solution library) as shown in FIG. 2 is formed, and respective liquids are flown in the flow channel converging part shown in FIG. 9 at respective constant flow rates, the group of drops 909 containing a reaction chemical solution, and the group of drops 910 not containing a reaction chemical solution are generated alternately, and the size of a drop containing a reaction chemical solution is larger than the size of a drop not containing a reaction chemical solution.

The quantity of oil between drops in the group of drops 909 generated in the state of FIG. 9A is smaller than the quantity of oil between drops in the group of drops 910 generated in the state of FIG. 9B. That is, the size of oil part is smaller.

These are determined according to the balance between the discharge of the aqueous solution and the discharge of oil at the time of generation of a drop at junction 904 or at junction 911 of flow channels. That is, as long as the flow channel converging part is configured as shown in FIG. 9A, and the discharge of the reaction chemical solution, the first oil, or the second oil relative to the sample solution is large, the size of drop 909 containing a reaction chemical solution is necessarily larger than the size of drop 910 not containing a reaction chemical solution by keeping the constant flow rates of the liquids flowing from the respective supply flow channels even if the discharges of the liquids from the respective supply flow channels are set differently. On the other hand, the size of oil in the group of drops 909 containing a reaction chemical solution is smaller than the size of oil in the group of drops 910 not containing a reaction chemical solution.

Also in the second exemplary embodiment, the group of drops containing a reaction chemical solution and the group of drops not containing a reaction chemical solution flow alternately, and the size of a drop containing a reaction chemical solution is larger than the size of a drop not containing a reaction chemical solution, and the size of oil in the group of drops containing a reaction chemical solution is smaller than the size of oil in the group of drops not containing a reaction chemical solution. Hence, it is possible to quantitatively analyze different kinds of nucleic acid targets by using the optical waveguide in the same manner as described in the first exemplary embodiment.

While the flow channel configuration shown in FIG. 9 has been described, the way of junction of flow channels is not limited to the form shown in these drawings, and any way of junction can be employed. For example, the first supply flow channel and the second supply flow channel may be connected at an angle of 90 degrees, and the third supply flow channel may be connected at an angle of 90 degrees. Changing the way of junction will not influence on the effect as long as the respective liquids are supplied from the first supply flow channel, the second supply flow channel, and the third supply flow channel at respective constant flow rates.

Example 1

In Example 1, a specific example using the flow channel converging part shown in FIG. 4 will be described. In the chemical solution tank, three different kinds of reaction chemical solutions A, B, C were retained with oil interposed therebetween. As the oil, an oil mix available from Biorad was used. The reaction chemical solution was prepared by mixing into a master mix available from Biorad as a base a primer and a fluorescent labeled probe that were suited for a desired nucleic acid target and were artificially made. The fluorescent labeled probe was prepared by mixing artificially made predetermined base sequences suited for each nucleic acid target, and the modified fluorescent dye was prepared by using the same Cy5 dye.

The microfluidic chip is configured by bonding the Si substrate and Pyrex (registered trademark) glass together by anode bonding, and the Si substrate is formed with an engraved flow channel of about 30 μm wide and 20 μm deep. A flow channel of the same size runs from the analyte supply port to the optical waveguide. Blood is injected through the analyte supply port, and mixed with a solvent composed of a buffer solution or the like in the pretreatment means, and then the resultant solution is heated to destroy cells, and thus nucleic acid that is to be examined is extracted. The sample solution containing the extracted nucleic acid is supplied to the flow channel converging part through the second supply flow channel of the flow channel converging part by means of a pump provided outside. The sample solution was supplied from the second supply flow channel at a constant flow rate of 5 nL/min.

The outlet of the chemical solution tank is connected with the reaction chemical solution supply port of the microfluidic chip, and the chemical solution is supplied through the first supply flow channel of the flow channel converging part at a constant flow rate by means of a pump provided outside. The flow rate was set at 75 nL/min.

Through the oil supply port of the microfluidic chip, an oil material that is identical to the oil enclosed in the chemical solution tank was supplied by means of a pump provided outside. The flow rate was set at 75 nL/min.

From three supply flow channels, the respective liquids were supplied to the flow channel converging part having the structure shown in FIG. 4, and drops were sequentially generated at the junction of flow channels.

First, reaction chemical solution A was supplied to the junction of flow channels. At this time, reaction chemical solution A flowing from the first supply flow channel at a flow rate of 75 nL/min, the sample solution flowing from the second supply flow channel at a flow rate of 5 nL/min, and oil flowing from the third supply flow channel at a flow rate of 75 nL/min converged at the junction of flow channels. The drop generated at this time was composed of a mixed solution of the sample solution and reaction chemical solution A, and a group of approximately 1000 drops was generated. The length of a drop containing reaction chemical solution A flowing in the flow channel was approximately 87±4 μm, and the length of an oil part between drops was approximately 23±1 μm. Calculation of the volume of a drop containing reaction chemical solution A from the length of the drop in the flow channel revealed that a group of drops having a size of 52±2 pL was formed.

Next, oil was supplied to the junction of flow channels from the first supply flow channel. At this time, oil flowing from the first supply flow channel at a flow rate of 75 nL/min, the sample solution flowing from the second supply flow channel at a flow rate of 5 nL/min, and oil flowing from the third supply flow channel at a flow rate of 75 nL/min converged at the junction of flow channels. The drop generated at this time was composed exclusively of the sample solution, and did not contain any reaction chemical solution. About 100 drops not containing a reaction chemical solution and composed of the sample solution were formed. The length of a drop containing a reaction chemical solution flowing in the flow channel was approximately 30±2 µm, and the length of an oil part between drops was approximately 80±3 µm. Calculation of the volume of a drop containing reaction chemical solution A from the length of the drop in the flow channel revealed that a group of drops having a size of 18±1 pL was formed.

Thereafter, in the same manner as described above, liquids were sequentially supplied from the first supply flow channel to the junction of flow channels at a flow rate of 75 nL/min in the order of reaction chemical solution B, oil, reaction chemical solution C, and oil. When reaction chemical solution B, C had reached the junction of flow channels, a group of drops of about 50 pL was formed likewise the case of reaction chemical solution A, and when oil had reached the junction of flow channels, a group of drops of about 20 pL was formed.

The drops generated in the flow channel converging part sequentially flow in the same order as they are generated, and were supplied to the PCR reactor. In Example 1, a PCR reactor formed in the range of 3 mm×6 mm was used. In the PCR reactor, a flow channel of 30 µm wide is arranged in such a manner that it is folded at intervals of 20 µm as shown in FIG. 5. The reactor has such an interior shape that 120 flow channels of about 3 mm long are arranged side by side. The PCR reactor can be heated or cooled at high speed by contact of a temperature control device using two Peltier elements having an area of 3 mm×3 mm from the side of the Si substrate. The PCR reactor is sequentially filled with the groups of drops generated in the flow channel converging part in the same order as they are generated. At the time of filling the PCR reactor with drops, valves provided in the inlet and the outlet of the PCR reactor are closed, and a nucleic acid amplification treatment by PCR is conducted. Here, a nucleic acid amplification treatment of 40 cycles, each cycle including 5 seconds at 90° C., 5 seconds at 57° C., and 5 seconds at 68° C. is conducted. In this process, the nucleic acid amplification treatment proceeds only in the drop containing a desired nucleic acid target, and the fluorescent dye is liberated in the drop. In a drop not containing a desired nucleic acid target, liberation of the fluorescent dye does not occur.

Thereafter, the valves in the inlet and the outlet of the PCR reactor are opened, and the drops are fed to the next optical waveguide in the same order as they are generated by means of a pump.

The optical waveguide in Example 1 was configured by using a semiconductor laser having a wavelength of 650 nm as a light source, and a current output type PMT as a fluorescent detector. The current output from the PMT was converted into a digital signal by using an AD converter, and the data was retrieved in a PC. From the acquired data, the crossing time of drop and the intensity of fluorescence are analyzed, and counting of the number of drops, counting of the number of drops emitting fluorescence and the like are conducted, and thus the content of the nucleic acid target is quantitatively analyzed. The object lens is fixed so that the drop passage position is irradiated with the laser light.

In counting the number of drops by the optical waveguide, drops were flown at a flow rate of approximately 400 nL/min by a pump provided outside. This flow rate allows counting of 100 drops per second.

FIG. 10 is a distribution chart showing the distribution of crossing time of a drop passing by the drop passage position. As illustrated in FIG. 1, the crossing time of a drop is obtained by setting the level of threshold 110 in an acquired output signal of the fluorescent detector, and measuring the time between the timing that the rising signal crosses threshold 110 and the timing that the falling signal crosses threshold 110 when a drop passes by. As illustrated in FIG. 10, the detected crossing times can be clearly separated into a group of 3 msec or less and a group of 7 msec or more. The drop having a crossing time of 7 msec or more is a drop containing a reaction chemical solution, and the drop having a crossing time of 3 msec or less is a drop not containing a reaction chemical solution. Since the drops pass by the drop passage position without disturbance of the order of generation, it is revealed that a large change point of crossing time is a boundary part between the group of drops containing a reaction chemical solution and the group of drops not containing a reaction chemical solution. Based on the change point of crossing time, it is possible to make analysis while separating the group of drops containing reaction chemical solution A, the group of drops containing reaction chemical solution B, and the group of drops containing reaction chemical solution C from one another. By analyzing the proportion of the number of fluorescent drops to the total number of drops in each group of drops, it is possible to determine to what extent nucleic acid targets are contained in the original sample.

Figure 11:
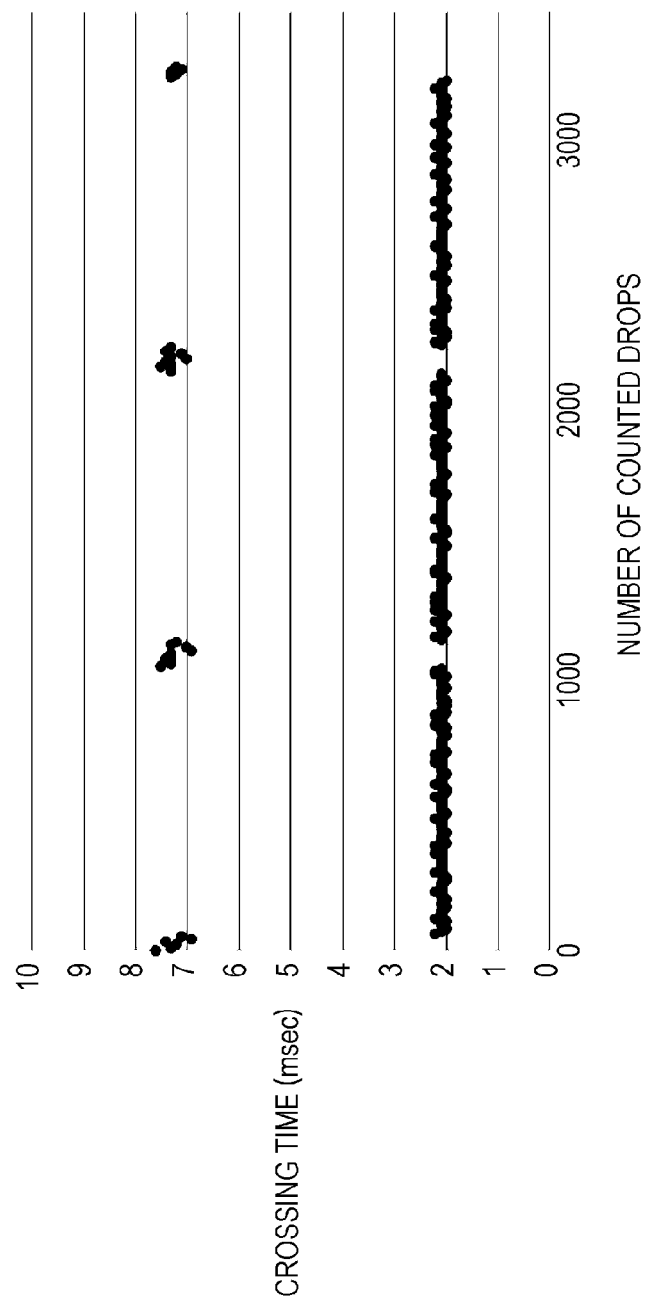
FIG. 11 is a distribution chart showing the distribution of crossing time of oil between drops in Example 1.

FIG. 11 is a distribution chart showing the crossing time of oil part between drops passing by the drop passage position. Contrarily to the case of drops, as shown in FIG. 8, the crossing time of oil is obtained by measuring the time between the timing that the falling signal crosses threshold 810, and the timing that the rising signal crosses threshold 810. As shown in FIG. 11, the crossing times of oil are also distributed clearly separately in a group of 6 msec or more and a group of 3 msec or less. Also with the crossing time of oil, it is possible to make analysis while clearly separating the group of drops containing reaction chemical solution A, the group of drops containing reaction chemical solution B, and the group of drops containing reaction chemical solution C from one another.

Figure 12:
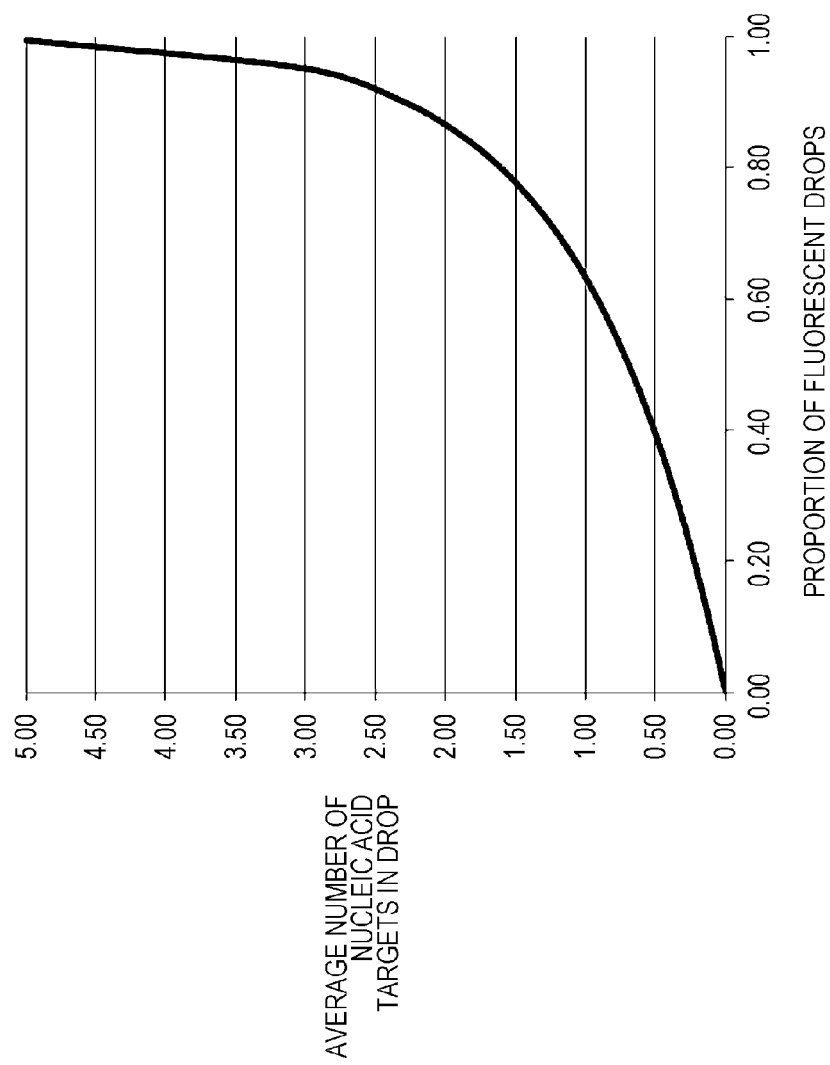
FIG. 12 is a graph showing a relation between proportion of fluorescent drops and an average number of nucleic acid targets in a drop.

Analysis of each reaction chemical solution is conducted in the following manner. In FIG. 10, a change point of crossing time of drop appears in the vicinity of around 50 drops from the starting of measurement. The drops included between this change point and the next change point (around 1050 drops from the starting of measurement) can be determined as a group of drops containing reaction chemical solution A. For the measured data of about 1000 drops included in this range, drops are counted by using the two threshold levels, threshold 110 and threshold 111 shown in FIG. 1. By counting the number of rising signals crossing threshold 110, it is possible to obtain the total number of drops containing reaction chemical solution A. Among these, by counting the number of times that the rising signal crosses threshold 111, it is possible to obtain the number of drops emitting fluorescence, namely drops containing a nucleic acid target to be detected and capable of reacting with reaction chemical solution A. In Example 1, the total number of drops containing reaction chemical solution A was 1005, and among these, the number of drops emitting fluorescence was 54. The proportion determined from the numbers of drops revealed that 5.4% of the drops contained a nucleic acid target. Since it is not unclear whether or not only one nucleic acid target is contained in one drop, the number of nucleic acid targets contained in one drop is estimated stochastically by adapting the idea of Poisson distribution. FIG. 12 is a graph showing the relation between the proportion of fluorescent drops and the average number of nucleic acid targets in a drop. As shown in FIG. 12, according to the idea of Poisson distribution, the number of nucleic acid targets contained in one drop can be estimated from the proportion of fluorescent drops to the total number of drops. In the case where the proportion of fluorescent drops is 5.4%, the number of nucleic acid targets contained in one drop is estimated as 0.056. Since the total number of drops containing reaction chemical solution A is 1005, it can be seen that the number of nucleic acid targets is 1005× 0.056=55.8. In other words, it can be found that in the volume of the sample solution used for generating 1005 drops, 55.8 nucleic acid targets reacting with reaction chemical solution A were contained.

By conducting the same process for reaction chemical solution B and reaction chemical solution C, it is possible to measure the quantity of nucleic acid targets with which the respective reaction chemical solutions react.

While the experiment was conducted for three kinds of reaction chemical solutions A, B, C, more than three reaction chemical solutions can also separately detected in a similar process.

Example 2

Figure 13:
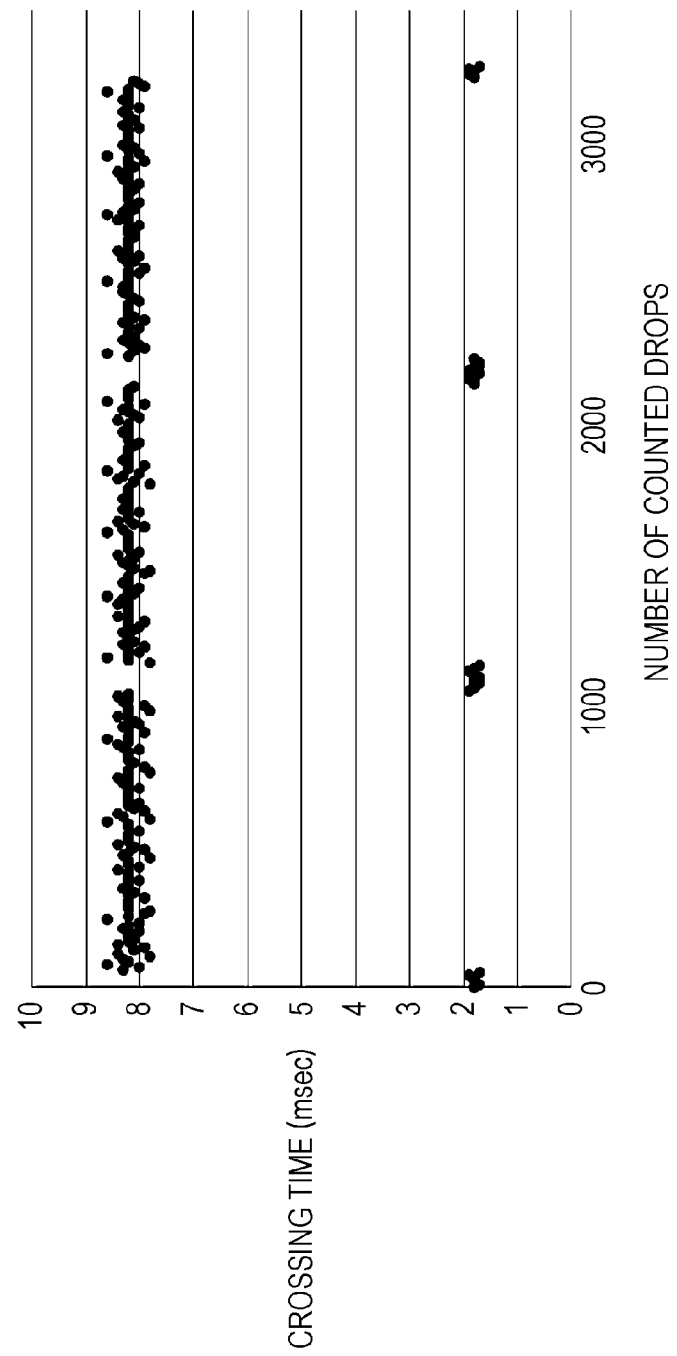
FIG. 13 is a distribution chart showing the distribution of crossing time of a drop in Example 2.
Figure 14:
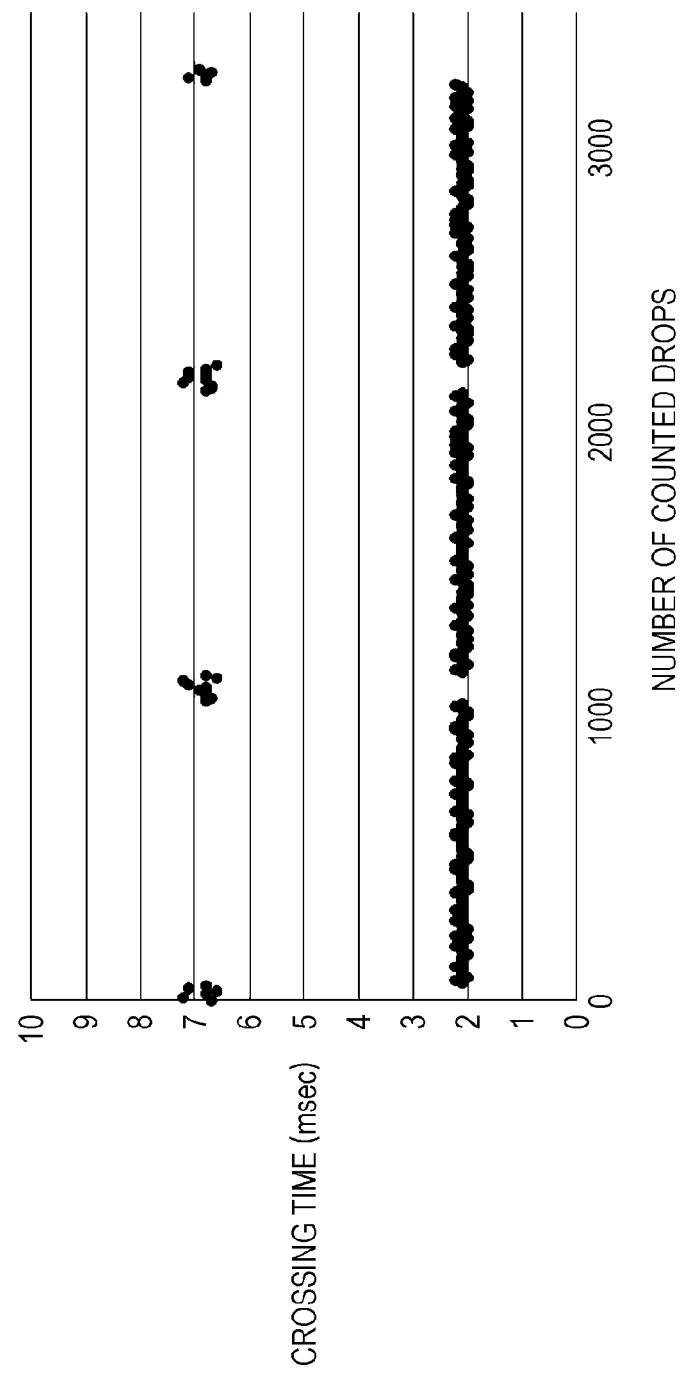
FIG. 14 is a distribution chart showing the distribution of crossing time of oil between drops in Example 2.

In Example 2, a specific example using the flow channel converging part shown in FIG. 9 will be described. Measurement was conducted in a similar condition as described in Example 1 except for the flow channel converging part. Similarly to Example 1, a crossing time of a drop and a crossing time of oil part between drops were measured. FIG. 13 is a distribution chart showing the distribution of crossing time of a drop. FIG. 14 is a distribution chart showing the distribution of crossing time of oil part between drops. In both of FIG. 13 and FIG. 14, a clear change point is observed in the distribution of crossing time. The change point is a boundary between the group of drops containing a reaction chemical solution and the group of drops not containing a reaction chemical solution. By obtaining the information of crossing time, it is possible to separately detect the groups of drops of respective reaction chemical solutions. Quantitative analysis of nucleic acid targets for each reaction chemical solution can be conducted in a similar process as in Example 1.

(Methods According to Various Aspects)

A method for analyzing multiple nucleic acid targets according to a first aspect is a method for analyzing multiple nucleic acid targets using a microfluidic chip, the chip including:

a first supply flow channel adapted for a first reaction chemical solution and a second reaction chemical solution that are modified with a fluorescent dye and react with different nucleic acid targets in on-to-one correspondence, and a first oil to flow;

a second supply flow channel adapted for a sample solution containing nucleic acid to flow;

a third supply flow channel adapted for a second oil to flow;

a fourth flow channel having one end that is a junction at which one end of the first supply flow channel, one end of the second supply flow channel, and one end of the third supply flow channel are connected;

a nucleic acid amplifier connected with another end of the fourth flow channel and conducts a treatment of amplifying nucleic acid;

a fifth flow channel connected with the nucleic acid amplifier and adapted for a drop in which the nucleic acid is amplified to flow; and an optical waveguide capable of taking out transmitted light that is transmitted through a drop flowing in the fifth flow channel, or taking out reflected light reflected after transmission through the drop outside, wherein by supplying the first reaction chemical solution, the first oil, and the second reaction chemical solution in this order from another end of the first flow channel, and supplying the sample solution containing nucleic acid from another end of the second supply flow channel, and supplying the second oil from another end of the third supply flow channel, the fourth flow channel is sequentially supplied with at least a first drop containing the first reaction chemical solution and the sample solution, a second drop containing the sample solution, a third drop containing the second reaction chemical solution and the sample solution, and a fourth drop containing the sample solution, the first drop to the fourth drop having flown in the fourth flow channel and reached the nucleic acid amplifier are amplified by the nucleic acid amplifier, when the first drop to the fourth drop amplified by the nucleic acid amplifier are flowing in the fifth flow channel, a size of a drop in the group of drops and an intensity of fluorescence of the drop are detected by the optical waveguide, a group of drops including the first drop and the third drop containing the reaction chemical solution with a size larger than or equal to a predetermined size is discriminated based on the size of the drop in the group of drops, and based on the intensity of fluorescence of the detected drop, it is analyzed that the sample solution is a target corresponding to a reaction chemical solution contained in a drop emitting fluorescence of an intensity of greater than or equal to a defined threshold among the first drop and the third drop containing the reaction chemical solution.

A method for analyzing multiple nucleic acid targets according to a second aspect includes:

a supplying step of supplying a reaction chemical solution and a first oil alternately to a first supply flow channel from a reaction chemical solution library including multiple reaction chemical solutions that are modified with a fluorescent dye and react with different nucleic acid targets in one-to-one correspondence, the multiple reaction chemical solutions being retained in a chemical solution tank formed of one flow channel while the multiple reaction chemical solutions are separated for each kind of the reaction chemical solutions via the first oil, supplying a sample solution containing nucleic acid to a second supply flow channel, and supplying a second oil to a third supply flow channel;

a drop generating step of converging the first supply flow channel, the second supply flow channel, and the third supply flow channel into one flow channel, and generating a group of drops containing the reaction chemical solution and a group of drops not containing the reaction chemical solution depending on a kind of liquid supplied from the first supply flow channel;

a nucleic acid amplifying step of introducing the drop and amplifying nucleic acid in the drop, a fluorescence detecting step of detecting fluorescence from a flowing group of drops, and detecting a size of a drop in the group of drops and an intensity of fluorescence of the drop;

a boundary detecting step of discriminating between a drop in the group of drops containing the reaction chemical solution and a drop in the group of drops not containing the reaction chemical solution based on the size of the drop in the group of drops, and acquiring a boundary between the group of drops containing the reaction chemical solution and the group of drops not containing the reaction chemical solution; and a counting step of counting a total number of drops and a number of drops emitting fluorescence larger than or equal to a defined threshold in the group of drops containing the reaction chemical solution separated and detected by the boundary.

A method for analyzing multiple nucleic acid targets according to a third aspect includes:

a supplying step of supplying a reaction chemical solution and a first oil alternately to a first supply flow channel from a reaction chemical solution library including multiple reaction chemical solutions that are modified with a fluorescent dye and react with different nucleic acid targets in one-to-one correspondence, the multiple reaction chemical solutions being retained in a chemical solution tank formed of one flow channel while the multiple reaction chemical solutions are separated for each kind of the reaction chemical solutions via the first oil, supplying a sample solution containing nucleic acid to a second supply flow channel, and supplying a second oil to a third supply flow channel;

a drop generating step of converging the first supply flow channel, the second supply flow channel, and the third supply flow channel into one flow channel, and generating a group of drops containing the reaction chemical solution and a group of drops not containing the reaction chemical solution depending on a kind of liquid supplied from the first supply flow channel;

a nucleic acid amplifying step of introducing the drop and amplifying nucleic acid in the drop, a fluorescence detecting step of detecting fluorescence from a flowing group of drops, and detecting a size of oil separating drops in the group of drops and an intensity of fluorescence of the drops;

a boundary detecting step of discriminating between the second oil that separates drops in the group of drops containing the reaction chemical solution and a mixture of the first oil and the second oil that separates drops in the group of drops not containing the reaction chemical solution based on the size of oil separating drops in the group of drops, and acquiring a boundary between the group of drops containing the reaction chemical solution and the group of drops not containing the reaction chemical solution; and a counting step of counting a total number of drops and a number of drops emitting fluorescence larger than or equal to a defined threshold in the group of drops containing the reaction chemical solution separated and detected by the boundary.

A method for analyzing multiple nucleic acid targets according to a fourth aspect includes:

a supplying step of supplying a reaction chemical solution and a first oil alternately to a first supply flow channel from a reaction chemical solution library including multiple reaction chemical solutions that are modified with a fluorescent dye and react with different nucleic acid targets in one-to-one correspondence, the multiple reaction chemical solutions being retained in a chemical solution tank formed of one flow channel while the multiple reaction chemical solutions are separated for each kind of the reaction chemical solutions via the first oil, supplying a sample solution containing nucleic acid to a second supply flow channel, and supplying a second oil to a third supply flow channel;

a drop generating step of converging the first supply flow channel and the second supply flow channel, and then converging the third supply flow channel into one flow channel, and generating a group of drops containing the reaction chemical solution and a group of drops not containing the reaction chemical solution depending on a kind of liquid supplied from the first supply flow channel;

a nucleic acid amplifying step of introducing the drop and amplifying nucleic acid in the drop;

a fluorescence detecting step of detecting fluorescence from a flowing group of drops, and detecting a size of a drop in the group of drops and an intensity of fluorescence of the drop;

a boundary detecting step of discriminating between a drop in the group of drops containing the reaction chemical solution and a drop in the group of drops not containing the reaction chemical solution based on the size of the drop in the group of drops, and acquiring a boundary between the group of drops containing the reaction chemical solution and the group of drops not containing the reaction chemical solution; and a counting step of counting a total number of drops and a number of drops emitting fluorescence larger than or equal to a defined threshold in the group of drops containing the reaction chemical solution separated and detected by the boundary.

In the method for analyzing multiple nucleic acid targets according to a fifth aspect, a size of a drop may be detected by a passing time of the drop in the flowing group of drops in the fluorescence detecting step in the second or the fourth aspect.

A method for analyzing multiple nucleic acid targets according to a sixth aspect includes:

a supplying step of supplying a reaction chemical solution and a first oil alternately to a first supply flow channel from a reaction chemical solution library including multiple reaction chemical solutions that are modified with a fluorescent dye and react with different nucleic acid targets in one-to-one correspondence, the multiple reaction chemical solutions being retained in a chemical solution tank formed of one flow channel while the multiple reaction chemical solutions are separated for each kind of the reaction chemical solutions via the first oil, supplying a sample solution containing nucleic acid to a second supply flow channel, and supplying a second oil to a third supply flow channel;

a drop generating step of converging the first supply flow channel and the second supply flow channel, and then converging the third supply flow channel into one flow channel, and generating a group of drops containing the reaction chemical solution and a group of drops not containing the reaction chemical solution depending on a kind of liquid supplied from the first supply flow channel;

a nucleic acid amplifying step of introducing the drop and amplifying nucleic acid in the drop;

a fluorescence detecting step of detecting fluorescence from a flowing group of drops, and detecting a size of oil separating drops in the group of drops and an intensity of fluorescence of the drops;

a boundary detecting step of discriminating between the second oil that separates drops in the group of drops containing the reaction chemical solution and a mixture of the first oil and the second oil that separates drops in the group of drops not containing the reaction chemical solution based on the size of oil separating drops in the group of drops, and acquiring a boundary between the group of drops containing the reaction chemical solution and the group of drops not containing the reaction chemical solution; and a counting step of counting a total number of drops and a number of drops emitting fluorescence larger than or equal to a defined threshold in the group of drops containing the reaction chemical solution separated and detected by the boundary.

In the method for analyzing multiple nucleic acid targets according to a seventh aspect, a size of oil may be detected by a passing time of the oil separating drops in the flowing group of drops in the fluorescence detecting step in the third or the sixth aspect.

In the method for analyzing multiple nucleic acid targets according to an eighth aspect, the first oil and the second oil may be formed of the same material in any of the first to seventh aspects.

In the method for analyzing multiple nucleic acid targets according to a ninth aspect, the first oil and the second oil may be formed of a single kind of material in any of the first to eighth aspects.

The method for analyzing multiple nucleic acid targets according to a tenth aspect may further include a light irradiation step of irradiating drops containing the modified nucleic acid flowing in the one flow channel in the same order as they are generated in any of the first to ninth aspects.

A microfluidic chip according to an eleventh aspect includes:

a flow channel converging part that converges, in one flow channel, a first supply flow channel to which a reaction chemical solution and a first oil are alternately supplied from a reaction chemical solution library including multiple reaction chemical solutions that are modified with a fluorescent dye and react with different nucleic acid targets in one-to-one correspondence, the multiple reaction chemical solutions being retained in a chemical solution tank formed of one flow channel while the multiple reaction chemical solutions are separated for each kind of the reaction chemical solutions via the first oil, a second supply flow channel to which a sample solution containing nucleic acid is supplied, and a third supply flow channel to which a second oil is supplied, and generates a group of drops containing the reaction chemical solution and a group of drops not containing the reaction chemical solution depending on a kind of liquid supplied from the first supply flow channel;

a nucleic acid amplifier to which the group of drops is introduced and in which nucleic acid in drops in the group of drops is amplified; and an optical waveguide capable of taking out transmitted light after transmission through drops containing the amplified nucleic acid flowing in the one flow channel in the same order as they are generated, or taking out reflected light reflected after transmission through the drops outside.

A device for analyzing nucleic acid targets according to a twelfth aspect is a device for analyzing nucleic acid targets that detects fluorescence from drops composed of a sample solution containing nucleic acid and reaction chemical solutions modified with a fluorescent dye and react with different nucleic acid targets in one-to-one correspondence, and detects a nucleic acid target, the device including:

a fluorescent detector that detects fluorescence from a group of drops containing the reaction chemical solution and a group of drops not containing the reaction chemical solution both flowing in one flow channel, and detects a size of a drop in the group of drops and an intensity of fluorescence of the drop;

a boundary detector that discriminates between a drop in the group of drops containing the reaction chemical solution and a drop in the group of drops not containing the reaction chemical solution based on the size of the drop in the group of drops, and acquires a boundary between the group of drops containing the reaction chemical solution and the group of drops not containing the reaction chemical solution; and a counter that counts a total number of drops and a number of drops emitting fluorescence larger than or equal to a defined threshold in the group of drops containing the reaction chemical solution separated and detected by the boundary.

The method for analyzing nucleic acid targets according to the present disclosure can be applied in a micro fluid device that quantitatively analyzes the quantity of nucleic acid targets to be analyzed from a sampled analyte such as blood. The method is particularly useful in simultaneously analyzing the contents of multiple nucleic acid targets to be analyzed. In the present disclosure, the flow channel configuration of the micro fluid device and the optical detection system for detecting fluorescence can be realized with very simple constitutions even in the case of simultaneously analyzing multiple nucleic acid targets, and hence it can be used in the site of tailor-made medical treatment and is particularly useful as a rapid and simple diagnosis device.

REFERENCE SINGS LIST 101 group of drops containing a reaction chemical solution
102 group of drops containing a reaction chemical solution
103 group of drops not containing a reaction chemical solution
104 group of drops not containing a reaction chemical solution
105 drop containing nucleic acid target and emitting fluorescence
106 drop not emitting fluorescence
107 optical signal from drop emitting fluorescence
108 optical signal from drop not emitting fluorescence
109 optical signal from drop not containing reaction chemical solution
110 threshold level for counting number of drops
111 threshold level for counting number of drops emitting fluorescence
112 crossing time of drop containing reaction chemical solution
113 crossing time of drop not containing reaction chemical solution
201 chemical solution tank
202 outlet of chemical solution tank
203 reaction chemical solution
204 first oil
205 air hole
301 base material such as Si substrate
302 glass plate
303 flow channel
304 microfluidic chip
305 pretreatment means
306 flow channel converging part
307 PCR reactor (nucleic acid amplifier)
308 optical waveguide
309 analyte supply port
310 reaction chemical solution supply port
311 oil supply port
401 first supply flow channel
402 second supply flow channel
403 third supply flow channel
404 junction of flow channels (one end of fourth flow channel)

405 reaction chemical solution
406 first oil
407 sample solution
408 second oil
409 drop containing reaction chemical solution
410 drop not containing reaction chemical solution
501 PCR reactor
502 gap
503 supply port
504 outlet
505 drop containing reaction chemical solution
506 drop not containing reaction chemical solution
601 single-stranded nucleic acid
602 single-stranded nucleic acid
603 forward primer
604 reverse primer
605 probe
606 fluorescent dye
607 quencher
700 microfluidic chip
701 base material such as Si substrate
702 glass plate
703 fifth flow channel
704 drop
705 laser
706 collimator
707 dichroic mirror
708 object lens
709 optical filter
710 lens
711 pinhole
712 PMT
801 group of drops containing reaction chemical solution
802 group of drops containing reaction chemical solution
803 group of drops not containing reaction chemical solution
804 group of drops not containing reaction chemical solution
805 drop containing nucleic acid target and emitting fluorescence
806 drop not emitting fluorescence
807 optical signal from drop emitting fluorescence
808 optical signal from drop not emitting fluorescence
809 optical signal from drop not containing reaction chemical solution
810 threshold level for counting number of drops
811 threshold level for counting number of drops emitting fluorescence
812 crossing time of drop containing reaction chemical solution
813 crossing time of drop not containing reaction chemical solution
901 first supply flow channel
902 second supply flow channel
903 third supply flow channel
904 junction of flow channels
905 reaction chemical solution
906 first oil
907 sample solution
908 second oil
909 drop containing reaction chemical solution
910 drop not containing reaction chemical solution
911 junction of flow channels

What is claimed is:

1. A method for detecting first nucleic acid targets and second nucleic acid targets using a microfluidic chip, the method comprising:
(a) installing the microfluidic chip in a detection device, wherein
the detection device comprises a PCR processor, a PCR reactor, a fluorescence detector, and a detect circuitry,
the microfluidic chip comprises a first flow channel, a second flow channel, a third flow channel, a fourth flow channel, and a fifth flow channel, wherein
the fourth flow channel is connected with one end of the first flow channel, one end of the second flow channel, and one end of the third flow channel,
the PCR reactor is located between the fourth flow channel and the fifth flow channel,
(b) (i) supplying from another end of the first flow channel a first aqueous solution, a first oil, and a second aqueous solution in this order, (ii) supplying from another end of the second flow channel a sample aqueous solution, and (iii) supplying a second oil from another end of the third flow channel, thereby causing a first drop, a second drop, a third drop and a fourth drop to pass through the fourth flow channel in this order, wherein
the first drop is made from the first aqueous solution and the sample aqueous solution,
the second drop is made from the sample aqueous solution,
the third drop is made from the second aqueous solution and the sample aqueous solution,
the fourth drop is made from the sample aqueous solution, wherein
the first aqueous solution has a first DNA having a complementary sequence to the first nucleic acid target, the first DNA is modified with a first fluorescent dye, and the second aqueous solution has a second DNA having a complementary sequence to the second nucleic acid target, the second DNA is modified with a second fluorescent dye,
(c) subjecting the first drop; the second drop; the third drop; and the fourth drop which have passed through the fourth flow channel and reached the PCR reactor, to a PCR process with the PCR processor, and causing the first drop; the second drop; the third drop; and the fourth drop which have been subjected to the PCR process to pass through the fifth flow channel,
(d) detecting intensities of fluorescence outputted from the first drop to the fourth drop flowing in the fifth flow channel with the fluorescence detector,
(e) acquiring boundaries between the first drop; the second drop; the third drop; and the fourth drop flowing in the fifth flow channel based on the intensities of fluorescence, and
(f) acquiring a number of the second drop and the fourth drop having an intensity of fluorescence greater than or equal to a first threshold based on the intensity of fluorescence and the boundaries between the first drop; the second drop; the third drop; and the fourth drop, and detecting whether or not the sample aqueous solution include at least one selected from the group consisting of the first nucleic acid target and the second nucleic acid target based on the number of the second drop and the fourth drop with the detect circuitry.

2. The method for detecting nucleic acid targets according to claim 1, wherein
in the step (b), (iv) a flow rate of the first aqueous solution, the first oil, and the second aqueous solution flowing in the first flow channel, (v) a flow rate of the sample aqueous solution flowing in the second flow channel, and (vi) a flow rate of the second oil flowing in the third flow channel are constant.

3. The method for detecting nucleic acid targets according to claim 1, wherein
one end of the fourth flow channel is connected with one end of the first flow channel, one end of the second flow channel, and one end of the third flow channel.

4. The method for detecting nucleic acid targets according to claim 1, wherein
one end of the fourth flow channel is connected with one end of the first flow channel, and one end of the second flow channel, and
one end of the third flow channel is connected between the one end and the other end of the fourth flow channel.

5. The method for detecting nucleic acid targets according to claim 1, wherein
in the step (d), a plurality of changes in intensity of fluorescence are detected, the plurality of changes in intensity of fluorescence is a change in intensity of fluorescence of greater than or equal to a second threshold, and
in the step (e), a plurality of boundaries are acquired as at least one boundary selected from the group consisting of (vii) a boundary between the first drop and the second drop, (viii) a boundary between the second drop and the third drop, (ix) a boundary between the third drop and the fourth drop, and (x) a boundary between the fourth drop and the first drop, based on each of positions where the plurality of changes in intensity of fluorescence are detected.

6. The method for detecting nucleic acid targets according to claim 5, wherein
the plurality of changes in intensity of fluorescence include a first change in the intensity of fluorescence and a second change in the intensity of fluorescence, and
in the step (e), boundaries between the first drop to the fourth drop are acquired by identifying the second drop and the fourth drop based on a time interval between a time when the first change in the intensity of fluorescence is detected and a time when the second change in the intensity of fluorescence is detected.

7. The method for detecting nucleic acid targets according to claim 6, wherein
in the step (e), when the time interval is longer than or equal to a predetermined time, a boundary corresponding to the second change in the intensity of fluorescence is acquired as (v) the boundary between the second drop and the third drop or (vii) the boundary between the fourth drop and the first drop.

8. The method for detecting nucleic acid targets according to claim 6, wherein
in the (e), when the time interval is shorter than a predetermined time, a boundary corresponding to the second change in the intensity of fluorescence is acquired as (iv) the boundary between the first drop and the second drop or (vi) the boundary between the third drop and the fourth drop.

9. The method for detecting nucleic acid targets according to claim 1, wherein
the first oil and the second oil are the same in material.

10. The method for detecting nucleic acid targets according to claim 1, wherein
the first fluorescent dye and the second fluorescent dye are the same in material.

11. The method for detecting nucleic acid targets according to claim 1, further comprising, between the step (c) and the step (d), a step of illuminating the first drop to the fourth drop flowing in the fifth flow channel with a light source.

12. A method for quantifying first nucleic acid targets and second nucleic acid targets using a microfluidic chip, the method comprising:
(a) installing the microfluidic chip in a quantitative device, wherein
the quantitative device comprises a PCR processor, a PCR reactor, a fluorescence detector, and a quantitative circuitry,
the microfluidic chip comprises a first flow channel, a second flow channel, a third flow channel, a fourth flow channel, and a fifth flow channel, wherein
the fourth flow channel is connected with one end of the first flow channel, one end of the second flow channel, and one end of the third flow channel,
the PCR reactor is located between the fourth flow channel and the fifth flow channel,
(b) (i) supplying from another end of the first flow channel a first aqueous solution, a first oil, and a second aqueous solution in this order, (ii) supplying from another end of the second flow channel a sample aqueous solution, and (iii) supplying a second oil from another end of the third flow channel, thereby causing a first drop, a second drop, a third drop and a fourth drop to pass through the fourth flow channel in this order, wherein
the first drop is made from the first aqueous solution and the sample aqueous solution,
the second drop is made from the sample aqueous solution,
the third drop is made from the second aqueous solution and the sample aqueous solution,
the fourth drop is made from the sample aqueous solution, wherein
the sample aqueous solution contains first nucleic acid targets and second nucleic acid targets,
the first aqueous solution has a first DNA having a complementary sequence to the first nucleic acid target, the first DNA is modified with a first fluorescent dye, and
the second aqueous solution has a second DNA having a complementary sequence to the second nucleic acid target, the second DNA is modified with a second fluorescent dye,
(c) subjecting the first drop; the second drop; the third drop; and the fourth drop which have passed through the fourth flow channel and reached the PCR reactor, to a PCR process with the PCR processor, and causing the first drop; the second drop; the third drop; and the fourth drop which have been subjected to the PCR process to pass through the fifth flow channel,
(d) detecting intensities of fluorescence outputted from the first drop to the fourth drop flowing in the fifth flow channel with the fluorescence detector,
(e) acquiring boundaries between the first drop; the second drop; the third drop; and the fourth drop flowing in the fifth flow channel based on the intensities of fluorescence, and
(f) acquiring a number of the second drop and the fourth drop having an intensity of fluorescence greater than or equal to a first threshold based on the intensity of fluorescence and the boundaries between the first drop; the second drop; the third drop; and the fourth drop, and quantifying the first nucleic acid targets and the second nucleic acid targets in the sample aqueous solution based on the number of the second drop and the fourth drop with the quantitative circuitry.

* * * * *